(12) United States Patent
Toyoshima et al.

(10) Patent No.: US 7,972,316 B2
(45) Date of Patent: Jul. 5, 2011

(54) DISPOSABLE DIAPER

(75) Inventors: Haruko Toyoshima, Tochigi (JP); Jun Sasaki, Tochigi (JP); Michiko Otsuka, Tokyo (JP); Mina Tomita, Tochigi (JP)

(73) Assignee: Kao Corporation, Tokyo (JP)

( * ) Notice: Subject to any disclaimer, the term of this patent is extended or adjusted under 35 U.S.C. 154(b) by 670 days.

(21) Appl. No.: 11/920,051

(22) PCT Filed: Apr. 18, 2006

(86) PCT No.: PCT/JP2006/308144
§ 371 (c)(1),
(2), (4) Date: Mar. 26, 2008

(87) PCT Pub. No.: WO2006/120847
PCT Pub. Date: Nov. 16, 2006

(65) Prior Publication Data
US 2009/0088718 A1 Apr. 2, 2009

(30) Foreign Application Priority Data

May 9, 2005 (JP) ................................. 2005-135625
Jul. 28, 2005 (JP) ................................. 2005-218146
Jul. 28, 2005 (JP) ................................. 2005-218450

(51) Int. Cl.
*A61F 13/15* (2006.01)
*A61F 13/20* (2006.01)

(52) U.S. Cl. ............... 604/385.01; 604/385.03; 604/367; 604/385.22

(58) Field of Classification Search ............. 604/385.01, 604/367, 378, 385.03
See application file for complete search history.

(56) References Cited

U.S. PATENT DOCUMENTS

| 5,916,206 | A | 6/1999 | Otsubo et al. |
| 6,673,982 | B1 * | 1/2004 | Chen et al. ..................... 604/378 |
| 7,744,579 | B2 * | 6/2010 | Langdon et al. ............... 604/386 |

(Continued)

FOREIGN PATENT DOCUMENTS

JP 6-421 U 1/1994

(Continued)

OTHER PUBLICATIONS

Chinese Office Action fir Application No. 200680015877.1 dated May 20, 2010.

*Primary Examiner* — Michele Kidwell
(74) *Attorney, Agent, or Firm* — Birch, Stewart, Kolasch & Birch, LLP

(57) ABSTRACT

A disposable diaper (1) has a waist opening portion and a pair of leg opening portions and contains an absorbent body including a topsheet and an absorbent core. The absorbent core (4) is composed of a central absorbent member (41) and a pair of side absorbent members (42) disposed on both sides of the central absorbent member (41). The central absorbent member (41) is discrete from the side absorbent members (42) in at least the crotch portion (C). Each side absorbent member has a raising elastic member which is provided near its outboard edge along the longitudinal direction, so that the side absorbent member (42) rises while worn. The diaper is configured to exert a higher wearing pressure in its regions (91) that are to be applied to a wearer's body part between the iliac crests and the anterior superior iliac spines than in its waist opening portion while worn.

7 Claims, 16 Drawing Sheets

U.S. PATENT DOCUMENTS

| | | |
|---|---|---|
| 2004/0122401 A1* | 6/2004 | Van Gompel et al. ... 604/385.14 |
| 2004/0243090 A1 | 12/2004 | Toyoshima et al. |
| 2005/0107763 A1 | 5/2005 | Matsuda et al. |
| 2005/0107764 A1* | 5/2005 | Matsuda et al. ............... 604/396 |

FOREIGN PATENT DOCUMENTS

| | | |
|---|---|---|
| JP | 7-28892 B2 | 4/1995 |
| JP | 9-84826 A | 3/1997 |
| JP | 10-5274 A | 1/1998 |
| JP | 2884355 B2 | 2/1999 |
| JP | 2001-340380 A | 12/2001 |
| JP | 2004-290646 A | 10/2004 |
| JP | 2005-65729 A | 3/2005 |

* cited by examiner

DISPOSABLE DIAPER

TECHNICAL FIELD

The present invention relates to a disposable diaper, particularly a pull-on (pants type) disposable diaper.

The present invention also relates to a disposable diaper that provides a neat appearance while worn and high leakage protection.

BACKGROUND ART

Pull-on diapers having an elastic member extensible in the diaper width direction disposed between the waist opening portion and leg opening portions are known. For example, JP 9-84826A proposes a pull-on disposable diaper, at least the stomach side of which has a first region defined at not exceeding 20 mm above and below the front end of the absorbent core and a second region defined between the first region and the leg opening portions. Elastic members are spacedly disposed in the first region at a smaller interval than in the second region. The proposal aims at leak prevention without impairing the wearing comfort by making the contact with the wearer's body better in the first region than in the second one while substantially equalizing the planar pressure per given area between the first and the second regions.

A pull-on disposable diaper having elastic members disposed at an interval gradually decreasing toward the leg opening is also known from JP U-6-421A. This configuration allows for a strong constrictive force being applied on the wearer's body part above the hipbone.

However, the above-described diapers are still liable to slide or slip down while worn to damage the appearance. The diaper further slides down with the wearer's movement and the weight of urine absorbed. As a result, the crotch portion of the diaper droops and becomes baggy, which tends to interfere with the wearer's movement. Moreover, the waist opening portion exerts a strong constrictive force which can make diapering difficult.

Conventional common pull-on disposable diapers tend to puff out and become baggy around the wearer's crotch while worn. The expression "become baggy" and the term "baggy" as used herein mean "be puffed out excessively". Baggy diapers interfere with the leg movement of the wearer. Baggy diapers easily get out of right position with the wearer's movement, which tends to cause a leak. Additionally, bagginess of a diaper makes it difficult to put outer clothing, such as shorts and pants, over the diaper only to provide a droopy appearance.

In order to eliminate bagginess of the crotch portion and to provide improved fit at the crotch portion, it is known as effective to have an absorbent member narrowed in the crotch portion. However, a diaper with such an absorbent member has reduced absorption capacity due to the substantially reduced width of its absorbent member in the crotch portion. The portion where the absorbent member is absent is incapable of absorbing bodily waste such as urine. As a result, leakage from the crotch portion easily occurs. The amount of a superabsorbent polymer to be disposed in the crotch portion could be increased to prevent leakage from the crotch portion. Although this configuration provides a good appearance and fit immediately after putting the diaper on a wearer, the crotch portion of the diaper after urine absorption is excessively puffed out due to the swell of the large amount of the polymer, which spoils the appearance.

Various proposals have been made in contemplation to provide both fit and leak protection in the crotch portion. For example, JP 7-28892B discloses a disposable diaper, in which the absorbent member is divided into three pieces; a first piece narrowed in the crotch portion and a pair of second pieces arranged on each lateral side of the narrowed part of the first piece with a gap from the first piece, the first piece being connected to each second piece by a hydrophilic sheet.

Diapers having the opposing second pieces of the three-divided absorbent member configured to rise have also been proposed. For example, JP 10-5274A discloses a disposable diaper, in which the absorbent member is divided into three pieces, a first piece narrowed in the crotch portion and a pair of second pieces arranged on each lateral side of the narrowed part of the first piece with a gap from the first piece, and a leak-preventive cuff having an elastic member along its free edge is provided on the long side portion of each second piece opposite to the first piece. The second pieces rise on both sides of the first piece away from the outermost sheet together with the respective leak-preventive cuffs.

Japanese Patent 2884355 proposes a disposable diaper having a first absorbent member laid flat in the longitudinally extending middle portion of the diaper and a second absorbent member laid on each lateral side of the first absorbent member with a spacing from at least part of the first absorbent member. An elastic member is disposed on the upper part of each second absorbent member to endow the second absorbent member with capability of gathering and rising.

The diaper design having an absorbent member divided into three sections in the crotch portion as disclosed in JP 7-28892B, JP 10-5274A, and JP 2884355 cited supra has a problem that the position where the side absorbent members rise is prone to unsteadiness while worn. Moreover, the central absorbent member disposed in the laterally middle portion of the diaper tends to have an unstable shape, being pressed inwardly by the risen side absorbent members. Therefore, fit and leakage protection in the crotch portion are hardly secured with this design.

The diaper having a leak-preventive cuff along the side of the rising side absorbent member as disclosed in JP 10-5274A can often allow the cuff to be untucked from the leg opening while worn.

DISCLOSURE OF THE INVENTION

The present invention provides a disposable diaper which while worn is kept from sliding down with the wearer's movement and sagging or drooping at the crotch portion with the weight of urine absorbed.

The present invention also provides a disposable diaper which while worn provides a good appearance, fit and leakage protection in the crotch portion thereof and keeps leak-preventive cuffs provided on both sides thereof from hanging out of the leg openings.

The present invention provides, in its first aspect, a disposable diaper including an absorbent body and having a waist opening portion and a pair of leg opening portion. The absorbent body includes a topsheet and an absorbent core. The absorbent core includes a central absorbent member and a pair of side absorbent members disposed on both sides of the central absorbent member. The central absorbent member is discrete from the pair of side absorbent members in at least the crotch portion of the diaper. Each of the side absorbent members has an elastic member for raising the side absorbent member (hereinafter sometimes referred to as a side absorbent member-raising elastic member) which is provided near the outboard edge thereof along the longitudinal direction, so that each side absorbent member is configured to rise while the diaper is worn. The diaper is configured to exert a higher pressure to the body of a wearer in its region adapted to be applied to a wearer's body part between the iliac crests and the anterior superior iliac spines than in the waist opening portion while worn.

The present invention also provides, in its second aspect, a disposable diaper including an absorbent body having a topsheet and an absorbent core. The absorbent core includes a central absorbent member and a pair of side absorbent members disposed on both sides of the central absorbent member. The central absorbent member is discrete from the pair of side absorbent members in at least the crotch portion of the diaper. The absorbent core has a side absorbent member-raising elastic member provided on both sides thereof along the longitudinal direction, so that the absorbent body is configured to raise both side portions thereof in the crotch portion thereof. The absorbent body has a leak-preventive cuff (hereinafter simply referred to as a cuff) provided on both sides thereof. The cuff includes a cuff-forming sheet joined to the absorbent body and a cuff-forming elastic member fixed in its stretched state to near the free edge of the cuff-forming sheet. The cuff further includes an elastic member for drawing the cuff (hereinafter sometimes referred to as a cuff-drawing elastic member) along a position outboard of the side absorbent member-raising elastic member in each lateral side of the diaper in its flat-out state.

DETAILED DESCRIPTION OF THE INVENTION

Figure 1:
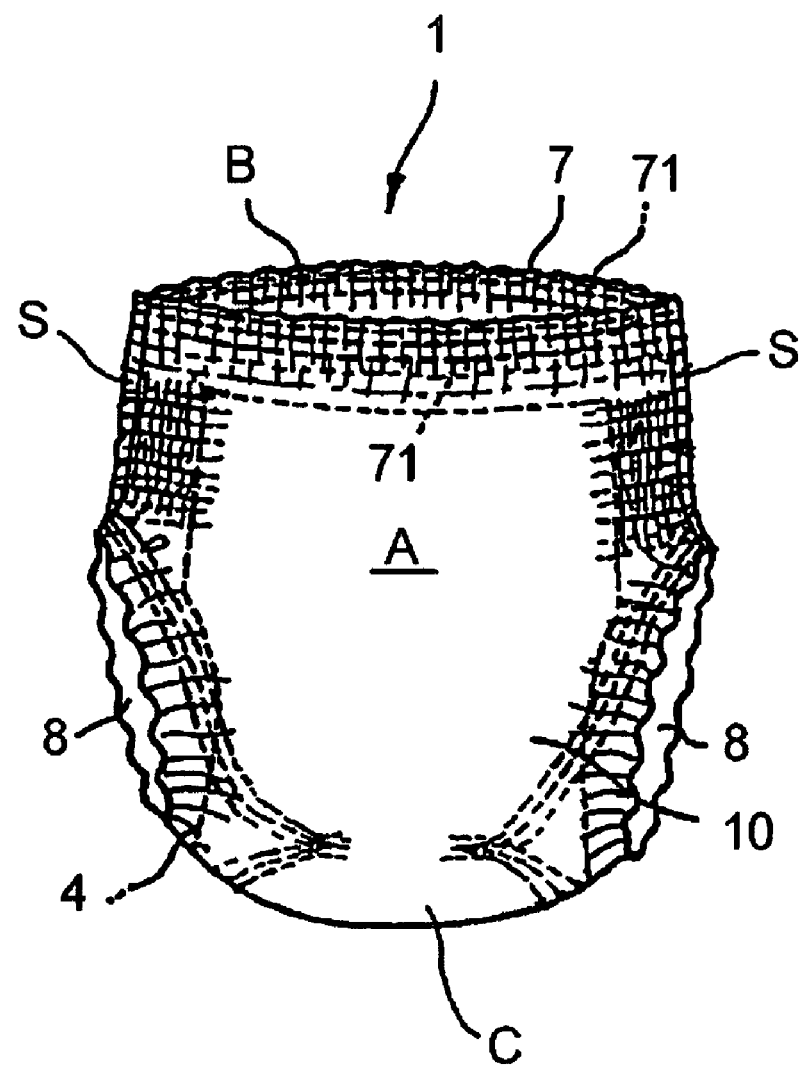
FIG. 1 is a perspective of an embodiment (first embodiment) of a pull-on disposable diaper according to the first aspect of the present invention.

The first aspect of the present invention will be described with reference to its preferred embodiment (first embodiment of the invention) by way of the accompanying drawing.

The disposable diaper 1 (hereinafter also referred to simply as "diaper 1") of the present embodiment is a so-called pull-on diaper. As shown in FIGS. 1 to 5, the diaper 1 includes an absorbent body 5 and an exterior laminate 10 on the garment-facing side of the absorbent body 5. The absorbent body 5 has a liquid permeable topsheet 2 and a liquid retentive absorbent core 4.

The diaper 1 is sectioned into a stomach portion A applied to the stomach side of a wearer, a back portion B applied to the back side of a wearer, and a crotch portion C positioned between the portions A and B while worn. The stomach portion A, back portion B, and crotch portion C of the diaper 1 correspond to approximately equal trisections along the longitudinal direction of the diaper 1 in its flat-out state shown in FIG. 2 with every elastic member stretched out (see FIG. 2).

As used herein, the term "garment facing side" denotes the opposite side of each member, such as an absorbent body, to the side that is to be directed to the skin of a wearer. The term "skin facing side" means the side of each member that is to face the skin of a wearer.

The absorbent body 5 has an oblong rectangular shape. It is bonded to a laterally middle portion of the exterior laminate 10 with its longitudinal direction coinciding with the longitudinal direction of the diaper to straddle the stomach portion A and the back portion B by means of known bonding means such as a hot-melt adhesive.

The exterior laminate 10 is joined to itself along both side edges of the stomach portion A and both side edges of the back portion B by any known means such as heat sealing, high frequency sealing or ultrasonic sealing thereby forming a pair of side seams S, a waist opening portion 7, and a pair of leg opening portions 8.

The aforementioned structure of the diaper 1 is the same as that of conventionally known diapers.

Figure 3A:
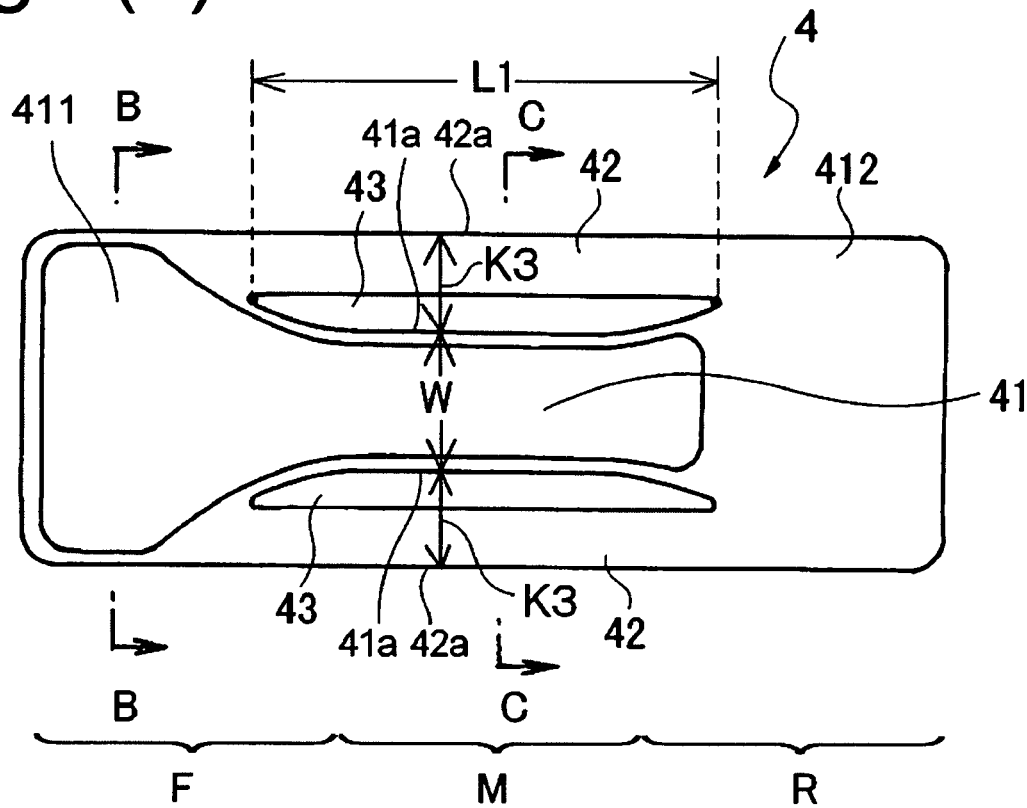
FIG. 3(a) is a plan of an absorbent core used in the diaper of FIG. 1.

As shown in FIG. 3(a), the absorbent core 4 used in the diaper 1 includes a central absorbent member 41 and a pair of side absorbent members 42 on both sides of the central absorbent member 41 in a symmetrical configuration. The central absorbent member 41 is discrete from the side absorbent members 42 in at least the crotch portion C. One longitudinal end portion and the other longitudinal end portion of each side absorbent member 42 are continuous with one longitudinal end portion F (hereinafter "front portion F") and the other longitudinal end portion R (hereinafter "rear portion R"), respectively, of the central absorbent member 41. Accordingly, a closed gap 43 is formed between the central absorbent member 41 and each of the pair of side absorbent members 42.

Figure 2:
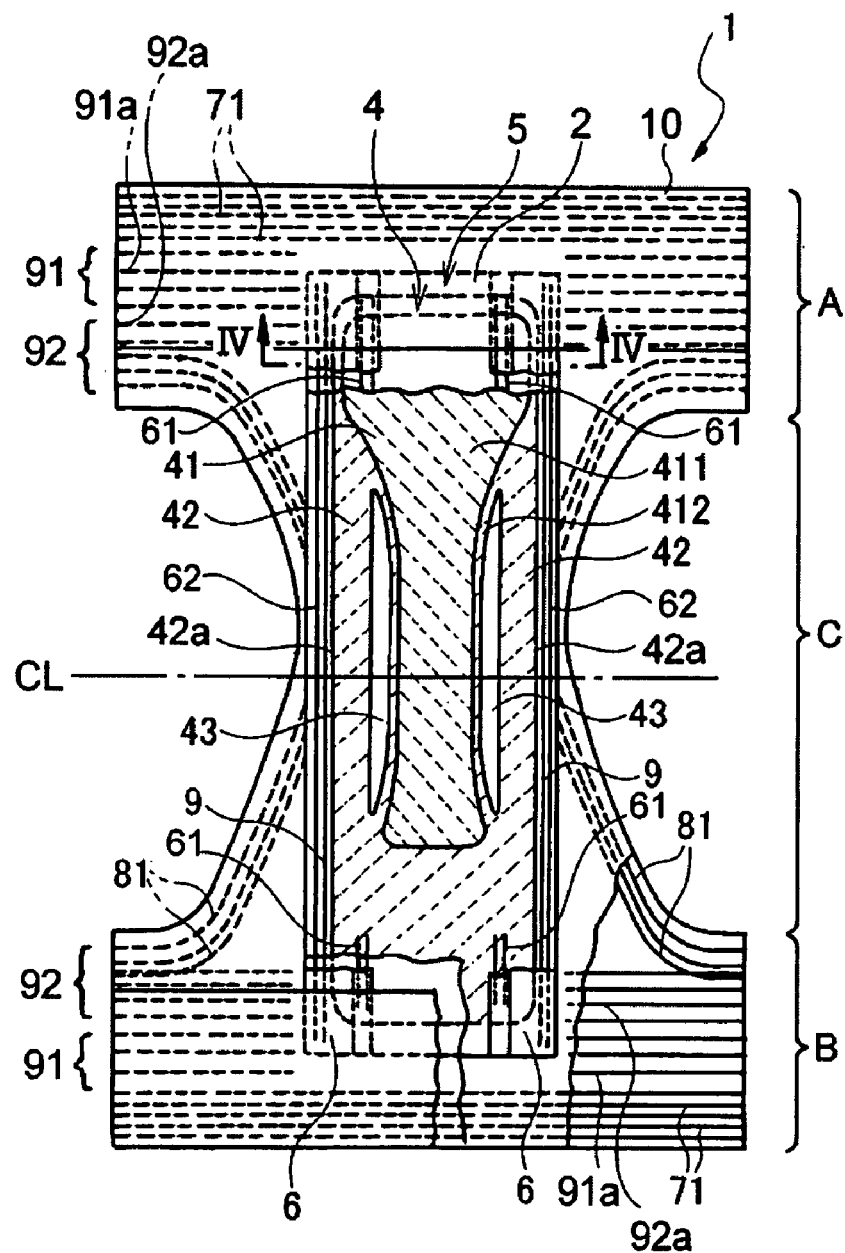
FIG. 2 is a plan of the diaper of FIG. 1 in its flat-out state, with the side seams cut open, every elastic member stretched out, and a part cut away.

As shown in FIGS. 2 and 3(a), the absorbent core 4 is disposed such that the side absorbent members 42 may be disposed in at least the crotch portion C of the diaper 1. In addition to this, the absorbent core 4 is configured such that the front portion F of the central absorbent member 41 may be located in the stomach portion A.

The front portion F, a longitudinally middle portion M (hereinafter "middle portion M"), and the rear portion R of the absorbent core 4 correspond to approximately one-third of the length of the absorbent core 4 shown in FIG. 3(a).

Figure 3B:
FIG. 3(b) is a cross-section taken along line B-B in FIG. 3(a).
Figure 3C:
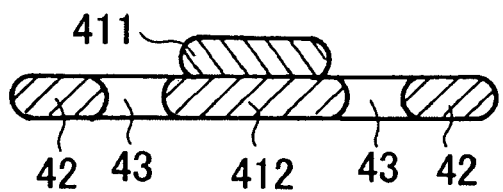
FIG. 3(c) is a cross-section taken along line C-C in FIG. 3(a).

As shown in FIGS. 3(a) to 3(c), the central absorbent member 41 is composed of a T-shaped upper absorbent submember 411 and a sandglass-shaped lower absorbent submember 412 larger than the upper absorbent submember 411. The upper absorbent submember 411 is superposed on the skin facing side of the lower absorbent submember 412 in a region straddling the front portion F and the middle portion M of the lower absorbent submember 412. The pair of side absorbent members 42 are integral with the lower absorbent submember 412. The upper absorbent submember 411 and the lower absorbent submember 412 are each made up of a mixture of a fibrous component such as pulp fiber and a superabsorbent polymer. The absorbent core 4 is totally wrapped in a water permeable cover sheet (not shown) formed of tissue paper or water permeable nonwoven fabric.

The diaper 1 has a side absorbent member-raising elastic member 9 disposed near the outboard edge 42a of each side absorbent member 42 along the longitudinal direction as shown in FIG. 2. With respect to the lateral position, the elastic member 9 is located between the topsheet 2 and the side edge face of the absorbent core 4. With respect to the longitudinal position, it is located to straddle the stomach portion A and the back portion B of the diaper. More specifically, the elastic member 9 is provided over the whole length of the absorbent core 4. The elastic member 9 is bonded to the adjacent topsheet 2 in its stretched state so that it will contract to raise the side absorbent member 42 while the diaper is in use.

Figure 4:
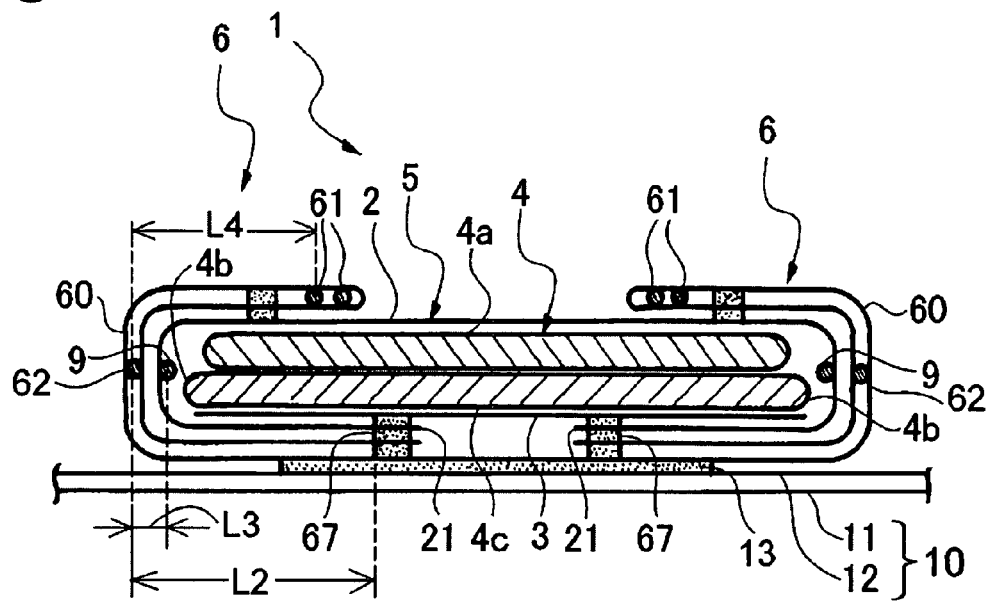
FIG. 4 is a schematic cross-section taken along line IV-IV in FIG. 2.
Figure 5:
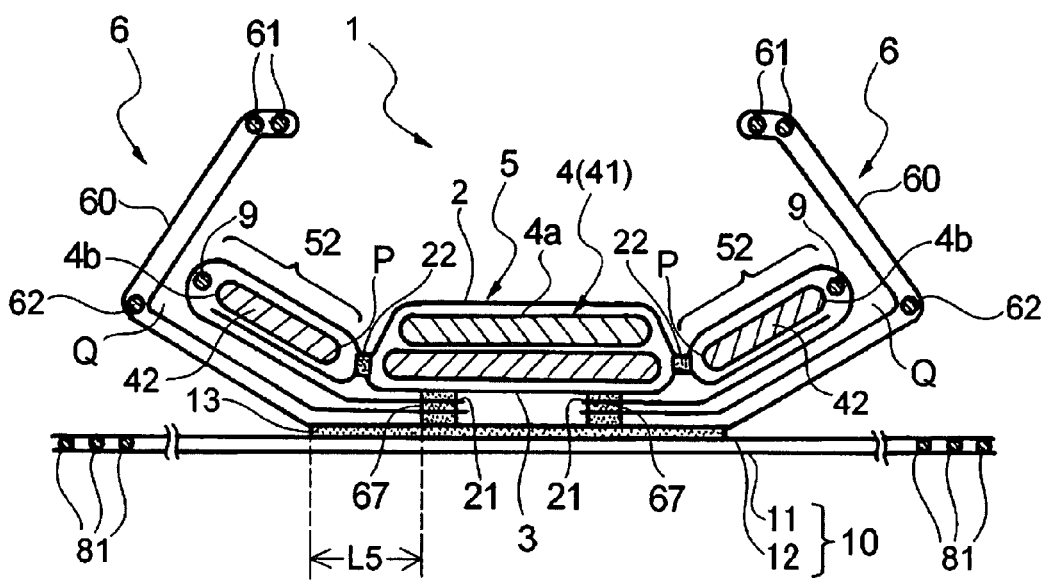
FIG. 5 is a schematic cross-section taken along line CL in FIG. 2.

As shown in FIGS. 2, 4, and 5, a pair of leak-preventive cuffs 6 are provided on both sides of the absorbent body 5. Each cuff 6 extends in the diaper's longitudinal direction. The cuff 6 includes a leak-preventive cuff-forming sheet 60 joined to the absorbent body 5, cuff-forming elastic members 61 fixed in their stretched state to near the free edge of the cuff-forming sheet 60, and an intermediate elastic member 62 fixed in its stretched state to a position intermediate the free edge and the fixed edge of the cuff 6.

While worn, the intermediate elastic members 62 contract to help the side absorbent members 42 to rise. The intermediate elastic members 62 also help the side absorbent members 42 to nest in the groins of wearer, which enhances the effect of preventing the crotch portion from sagging due to the presence of the side absorbent members 42. The cuff-forming elastic members 61 contract to cause the side absorbent members 42 to rise and nest in the wearer's groins thereby providing improved leakage protection.

The elastic members 9 and the intermediate elastic members 62 are preferably aligned with each other along the respective sides of the absorbent body 5 in a flat-out state of the diaper 1 as shown in FIG. 4.

A dual layer sheet is used as a cuff-forming sheet 60 in the diaper 1. The dual layer sheet is formed by folding a water repellent strip of prescribed width in two along a longitudinal folding line and joining the facing two panels with a hot-melt adhesive or partial heat or ultrasonic sealing, etc. The cuff-forming elastic members 61 are fixed in their stretched state between the facing panels.

The topsheet 2 of the diaper 1 covers the entire area of the skin facing side 4a of the absorbent core 4, the entire area of both lateral side edge faces 4b of the absorbent core 4, and both lateral side portions and their vicinities of the garment facing side 4c of the absorbent core 4 as shown in FIGS. 4 and 5. Both side edge portions 21 of the topsheet 2 cover part of the garment facing side of the central absorbent member 41. The absorbent body 5 of the diaper 1 has a liquid impermeable backsheet 3 that covers the entire area of the garment facing side 4c of the absorbent core 4. The backsheet 3 is fixedly held between the absorbent core 4 and the portions of the topsheet 2 that cover the lateral side portions and their vicinities of the garment facing side 4c of the absorbent core 4.

The topsheet 2 is fixed on its side edge portions 21 to the backsheet 3 and the cuff-forming sheets 60 by joining means such as heat sealing to form absorbent body joints 67. Each absorbent body joint 67 is located inward in the width direction of the diaper of the most inner side of position of the inboard edge of the side absorbent member 42 as shown in FIG. 5. The absorbent body joints 67 are formed by joining the cuff-forming sheets 60, the side edge portions 21 of the topsheet 2, and the backsheet 3 by known joining means such as heat sealing, high frequency sealing, ultrasonic sealing or application of a hot-melt adhesive.

The topsheet 2 covering the skin facing side 4a of the absorbent core 4 and the backsheet 3 covering the garment facing side 4c of the absorbent core 4 are also joined to each other in the gaps 43 of the absorbent core 4 in the crotch portion to form topsheet/backsheet joint 22 as shown in FIG. 5. Since the gaps 43 are covered with the cover sheet (not shown) as stated above, the topsheet 2 and the backsheet 3 are bonded via the cover sheet.

To the skin facing side of the exterior laminate 10 are bonded the cuff-forming sheets 60 and the absorbent body 5 in that order. The cuff-forming sheets 60 are bonded to the exterior laminate 10 via a joint 13. The outboard edges of the joint 13 are laterally outboard of the absorbent body joints 67.

The exterior laminate 10 has at least two sheets of nonwoven fabric, i.e., an outer nonwoven sheet 11 and an inner nonwoven sheet 12 disposed on the inner side of the outer nonwoven sheet 11 as shown in FIGS. 2, 4, and 5. The outer nonwoven sheet 11 defines the outer surface of the diaper 1. The inner nonwoven sheet 12 is joined to the inner side of the outer nonwoven sheet 11 with an adhesive, such as a hot-melt adhesive. The outer nonwoven sheet 11 extends outward from the front and rear ends (both longitudinal ends) of the inner nonwoven sheet 12, and the extensions are folded back over the absorbent body 5 to cover the front and rear portions of the absorbent body 5 (i.e., the longitudinal end portions of the topsheet 2).

Figure 6:
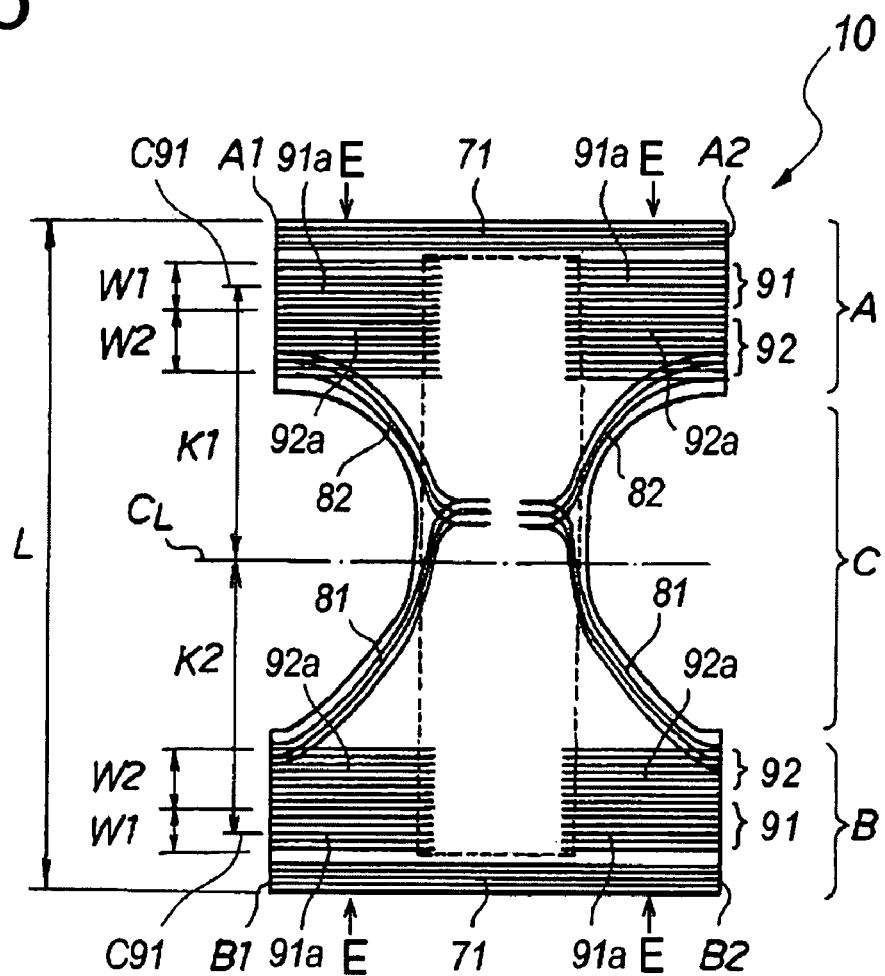
FIG. 6 is a plan of an exterior laminate shown in FIG. 2 in its flat-out state.

A plurality of waist elastic members 71 are disposed along the front and the rear ends of the exterior laminate 10 over the entire width of the ends as shown in FIG. 6. Each waist elastic member 71 is fixed between the outer nonwoven sheet 11 and the inner nonwoven sheet 12 in its stretched state. The waist elastic members 71 are arranged such that those on the stomach portion A and those on the back portion B overlap with each other at their ends or such that their ends continuously extend up to the side seams when the side edges A1 and A2 of the stomach portion A and the side edges B1 and B2 of the back portion B are joined together. As a result, a substantially continuous loop of waist gather is formed along the waist opening portion 7 of the diaper 1 as shown in FIG. 1.

Leg elastic members 81 and 82 are disposed in the curved portions on both sides of the exterior laminate 10. Each of the leg elastic members 81 and 82 is disposed along the curved edge. The leg elastic members 81 and 82 are sandwiched between the outer nonwoven sheet 11 and the inner nonwoven sheet 12 and fixed in their stretched state by a prescribed joining means. The leg elastic members 81 and 82 overlap at one of their ends in the crotch portion C. The other end of each of the leg elastic members 81 and 82 is located at the side edge of the back portion B and the side edge of the stomach portion A, respectively.

The leg elastic members 81 and 82 are arranged such that their ends overlap with each other or such that their ends continuously extend up to the side seams when the side edges A1 and A2 of the stomach portion A and the side edges B1 and B2 of the back portion B are joined together. As a result, a substantially continuous loop of leg gather is formed near each leg opening portion 8 of the diaper 1 as shown in FIG. 1.

The diaper 1 has a number of elastic members extending in the width direction of the diaper between the waist opening portion 7 and the leg opening portions 8 in each of the stomach portion A and the back portion B. By disposing the elastic members, a first region 91 and a second region 92 are formed both extending transversely of the diaper 1 as shown in FIG. 6. First elastic members 91a are disposed in the first region 91, and second elastic members 92a are disposed in the second region 92. The first region 91 is positioned between the waist opening portion 7 and leg opening portions 8, and the second region 92 is positioned between the first region 91 and the leg opening portions 8.

All the first elastic members 91a and the second elastic members 92a are fixed in their stretched state between the outer nonwoven sheet 11 and the inner nonwoven sheet 12. The first elastic members 91a are arranged such that, when the side edges A1 and A2 of the stomach portion A and the side edges B1 and B2 of the back portion B are joined together, the ends of the first elastic members 91a of the stomach portion A and the ends of the first elastic members 91a of the back portion B overlap with each other or that the end of every elastic member 91a extends up to the side seam. The same applies to the arrangement of the second elastic members 92a.

Each of the first elastic members 91a and the second elastic members 92a extends between a lateral side edge of the diaper 1 (i.e., a lateral side edge of the exterior laminate 10) and a lateral, long side edge of the absorbent core 4 on each lateral side of the diaper 1. None of the first elastic members 91a and the second elastic members 92a substantially exists in the area where the absorbent core 4 exists. That is, the gathers formed in the first region 91 and the second region 92 are located between each side seam of the diaper 1 and each lateral side edges of the absorbent core 4. There is substantially no gather in the area where the absorbent core 4 is disposed. Therefore, contraction of the exterior laminate 10 due to contraction of the first elastic members 91a and the second elastic members 92a does not occur in the area where the absorbent core 4 exists while worn, so that the diaper 1 not only keeps its neat appearance but secures satisfactory absorption performance.

The elastic members used in the diaper 1 according to the present embodiment preferably include stretch materials, such as natural rubber, polyurethane resins, foamed urethane resins, stretch nonwoven fabrics, and hot-melt stretch materials, molded into a string, a tape, a net or film.

Figure 7:
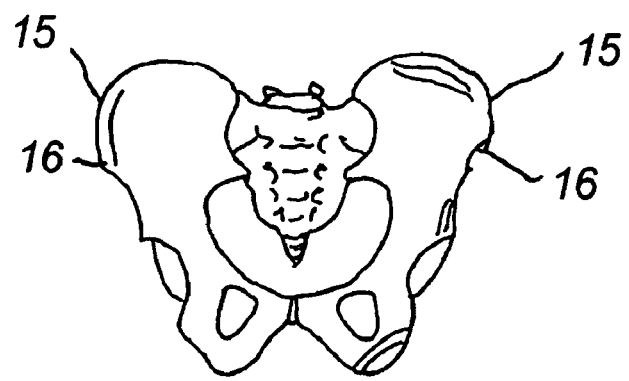
FIG. 7 is an illustration of the ilia.

According to the present embodiment, the pressure exerted on the wearer's body by the first region 91 is controlled within a range of from 1.1 to 2.5 kPa. The first region 91 is preferably formed in the region of the diaper 1 which, while worn by a wearer, is applied to a wearer's body part between the left and right iliac crests and the left and right anterior superior iliac spines. That part of a wearer's body will sometimes be referred to as the iliac region. The anatomical terms "iliac crest" and "anterior superior iliac spine" refer to the sites indicated by the reference numerals 15 and 16, respectively, in FIG. 7.

In order to prevent a pull-on diaper from sliding down, particularly to prevent a pull-on diaper worn by a child from sliding down, it has been considered effective to increase the constrictive pressure of the elastic members disposed in the waist opening portion thus bringing the pull-on diaper into close contact with a wearer's body as exemplified by the design of JP U-6-421A supra.

In contrast, as a result of investigation seeking for a solution of the problem that a pull-on diaper tends to slide down while worn, the present inventors have found it more effective to increase the constrictive pressure of the portion corresponding to the wearer's iliac region than to increase the constrictive pressure of the waist opening portion. The reason is as follows. Because a diaper wearer, especially a child has a protruding abdomen as a physical characteristic, an increased constrictive pressure of the waist of a pull-on diaper applied around the protruding belly gradually makes the waist of the diaper to constrict, thereby causing the diaper to slide down until it fits a less protruding part of the belly.

Figure 8:
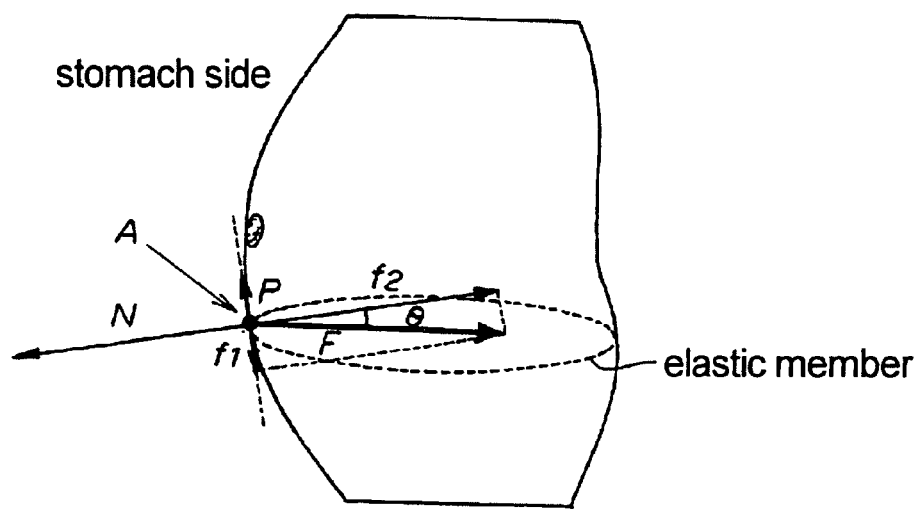
FIG. 8 illustrates how to calculate the sliding force around the waist of a wearer.

FIG. 8 is an illustration of a child's abdomen comparing a child's body to a circular cone. In FIG. 8, $\theta$ is an angle between a normal to the tangent at a waist point (point A) and a horizon directing to the center of the body; F represents a constrictive force of an elastic body; P represents a frictional force attributed to the constrictive force F; f1 represents a sliding force attributed to the constrictive force F; and f2 represents a normal force. $f1 = F \sin \theta$, and $P = \nu N = \nu f2 = \nu F \cos$ θ (where ν represents a coefficient of friction). Accordingly, a downward sliding force Z at point A is represented by equality:

$$Z = f1 - P = F\sin\theta - \nu F\cos\theta = F(\sin\theta - \nu\cos\theta)$$

It is understood from the equality above that a larger constrictive force (F) creates a larger sliding force when the waist of a diaper is in a state ready to slide down.

As stated previously, the pressure of the first region 91 exerted while the diaper 1 is worn is from 1.1 to 2.5 kPa. If that pressure is less than 1.1 kPa, it is difficult to keep the first region 91 on the iliac region of the wearer, and the diaper 1 easily moves down, resulting in a dull, droopy appearance. Drooping of the diaper 1 is conspicuous particularly around the crotch C, thus causing urine and fecal leakage.

If that pressure is more than 2.5 kPa, on the other hand, the diaper 1 will not only constrict the wearer's body too strong but also be difficult to put on a wearer. To further ensure the prevention of the diaper 1 from sliding down, to improve the appearance of the diaper 1 while worn, and to facilitate diapering, it is preferred that the pressure of the first region 91 while worn range from 1.1 to 2.0 kPa, more preferably from 1.2 to 1.8 kPa.

The pressure exerted by the first region 91 of the diaper 1 while worn is adjustable by selecting the material, thickness, elongation, and the spacing of the first elastic members 91a.

Measurement of the pressure of the first region 91 of the diaper 1 is carried out on the diaper 1 put on a cylinder having a circumference of 500 mm with a clothing pressure measuring device (air-pack type contact surface pressure measuring system AMI 3037-2, available from AMI Techno Co., Ltd.) as follows.

Measurement of Pressure by First Region 91:

An air pack (pressure sensor) having a diameter of 15 mm is placed with its center aligned with the waist opening edge of the diaper, and the wearing pressure value P1 is measured. The air pack setting position in the width direction of the diaper is nearly the middle between each lateral side edge of the diaper and each lateral side edge of the absorbent core 4 (indicated by letter E in FIG. 6). Subsequently, the air pack is shifted down by 5 mm along the diaper length direction to measure the pressure value P2. The same measurement is repeated at 5 mm interval to obtain pressure values P3, P4, P5 . . . , and Pn. The measurements for obtaining P1 to Pn are made within a region where the lateral side edges of the exterior laminate 10 are joined to each other between the waist opening and the leg openings. The measurement is conducted at four points at every vertical position in each of the stomach portion A and the back portion B, two in the left side and two in the right side, to obtain an average pressure at a specific vertical position of the stomach portion A or the back portion B.

The vertical distance between two out of the n sites of measurement between which all the measured pressure values P are within a range of 1.1 kPa and 2.5 kPa is taken as the width of the first region 91. When, for instance, values from P3 to P6 fall within the recited range, the width of the first region 91 is (6−3)×5=15 mm. In that case, the mid point between the measuring site of P3 and that of P6 is the widthwise middle of the first region 91.

The mean circumference of the waist of children at which the diaper 1 of the present embodiment is primarily targeted is about 500 mm, which is selected as the diameter of the cylinder. The term "circumference of the waist" as used herein is an average of the circumference measured of a child in a standing posture and that of the child in a sitting posture, taking into consideration a probable change in the circumference at the waist with the change in body posture. In the case of diapers for adults, the cylinder with circumference 500 mm is replaced with a cylinder with circumference 850 mm.

There is a certain distance between the iliac crest and the anterior superior iliac spine of a wearer, i.e., width of the iliac region. The diaper 1 is effectively kept from moving down by applying the first region 91 of the diaper 1 to a body part within that width of the iliac region. From this point of view, the first region 91 of the diaper 1 according to the present embodiment preferably has a width W1 (see FIG. 6), measured in the diaper length direction, of 12 to 35 mm. With the width W1 being 20 to 35 mm, more desirably 25 to 30 mm, the diaper 1 will be kept in place more effectively, and the appearance of the diaper 1 while worn and the ease of diapering performance of the diaper 1 will be further improved.

In order for the first region 91 to be applied to the wearer's body part between the iliac crest and the anterior superior iliac spine, the relation between the size of the diaper 1 and the physical size of a wearer is of importance. Considering children, primarily targeted wearers, for instance, the first region 91 can successfully be applied to the iliac region of a wearer when the distance K1 (see FIG. 6) from the widthwise middle of the first region 91 (i.e., the middle of the first region 91 along the diaper length direction) of the stomach portion A to the centerline CL along the lateral direction of the diaper 1 is 180 to 230 mm as measured in the flat-out state of the diaper 1, and also when the distance K2 (see FIG. 6) from the widthwise middle of the first region 91 (i.e., the middle of the first region 91 along the diaper length direction) of the back portion B to the centerline CL of the diaper 1 is 180 to 230 mm as measured in the flat-out state of the diaper 1.

Figure 9:
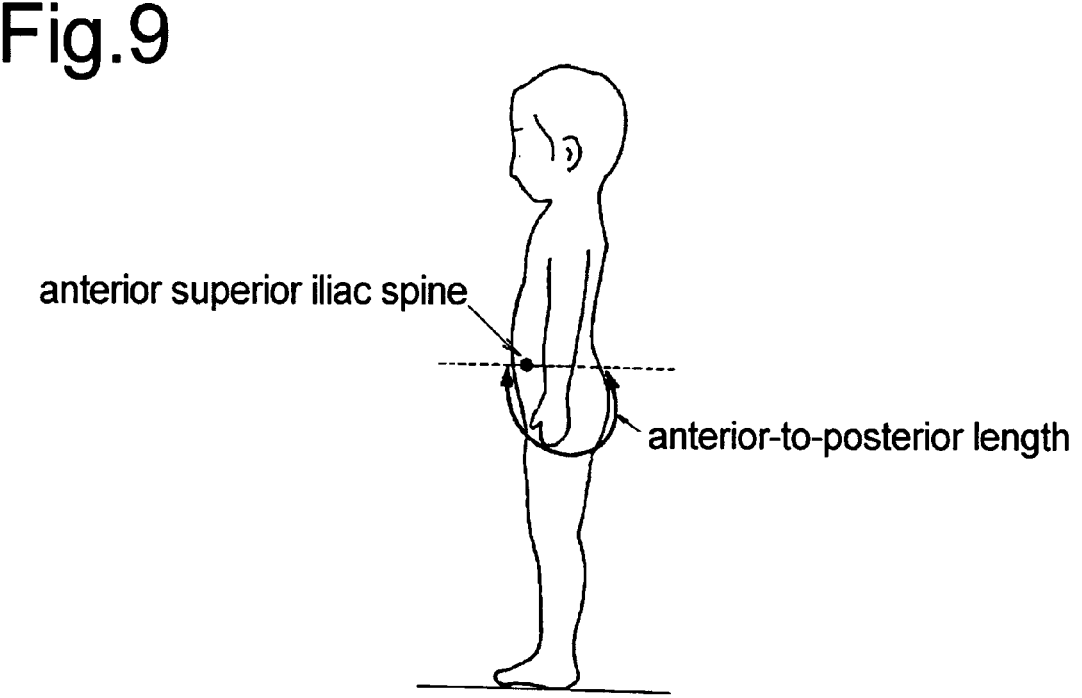
FIG. 9 illustrates how to measure the anterior-to-posterior length at the height of the anterior superior iliac spine.

The recited K1 and K2 values have been decided as a result of body measurement of about 350 children for whom pull-on type diapers are primarily designed. These values will be described more specifically by referring to FIG. 9. The mid point between, and at the height of, the left and right anterior superior iliac spines in the anterior view of a child is designated "anterior center". The mid point similarly defined but in the posterior view of the child is designated "posterior center". The length from the anterior center via the crotch to the posterior center is designated "anterior-to-posterior length". The sum of the anterior-to-posterior length and an allowance for the thickness of the diaper materials and the like is divided by two to give the above-recited K1 and K2 values. In order to apply the first regions 91 to the iliac region of a wearer more successfully, the distances K1 and K2 are more preferably 185 to 220 mm, even more preferably 195 to 215 mm. For designing diapers for adults, the first regions 91 will be applied to the iliac region of an adult wearer more successively by adjusting the K1 and K2 values preferably to a range of 300 to 350 mm, more preferably 305 to 335 mm.

The first region 91 exists in each of the stomach portion A and the back portion B. The wearing pressure of the first region 91 in the stomach portion A and that of the back portion B do not need to be exactly equal. As long as the pressure of each of the first regions 91 in the stomach portion A and the back portion B is in a range of from 1.1 to 2.5 kPa, the elastic members arranged on the stomach side and those on the back side of the diaper may differ in material, thickness, elongation, and distance of spacing. Nevertheless, excessive configurational difference between the first region 91 of the stomach portion A and that of the back portion B can result in a dull appearance of the diaper because the side seams of the exterior laminate 10 may come to the front or rear side of the diaper worn. Hence, it is desirable that the ratio of the difference between a higher one, taken as A, of two pressure values of the first region 91 on the stomach portion A and the back portion B and a lower one, taken as B, to the higher one, i.e., (A−B)/A, be within 30%.

Where the diaper 1 of the present invention has its stomach portion A and the back portion B joined together with the side edges A1 and A2 of the former and the side edges B1 and B2 of the latter substantially coinciding with each other; the term "centerline CL" as used in the present invention refers to the straight line parallel to the diaper width direction and passing the mid point between A1 and B1 of the diaper 1 in the flat-out state (see FIG. 6).

Figure 10A:
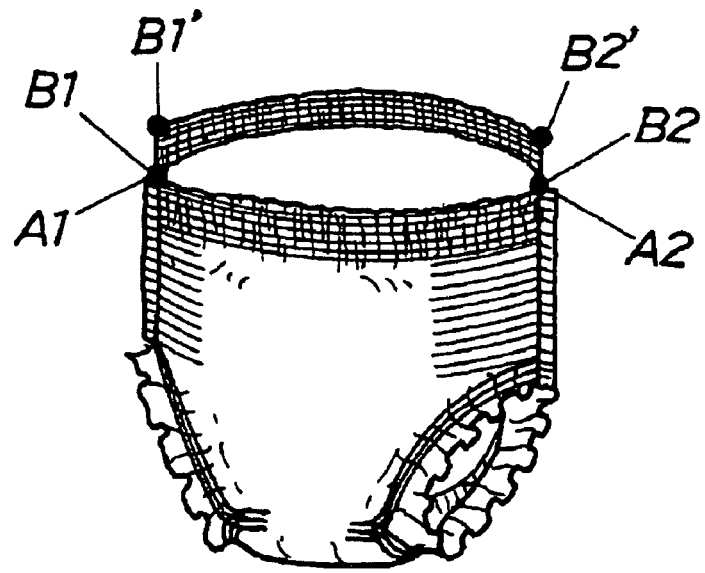
FIG. 10(a) is a perspective illustrating another embodiment of the diaper according to the first aspect of the present invention.
Figure 10B:
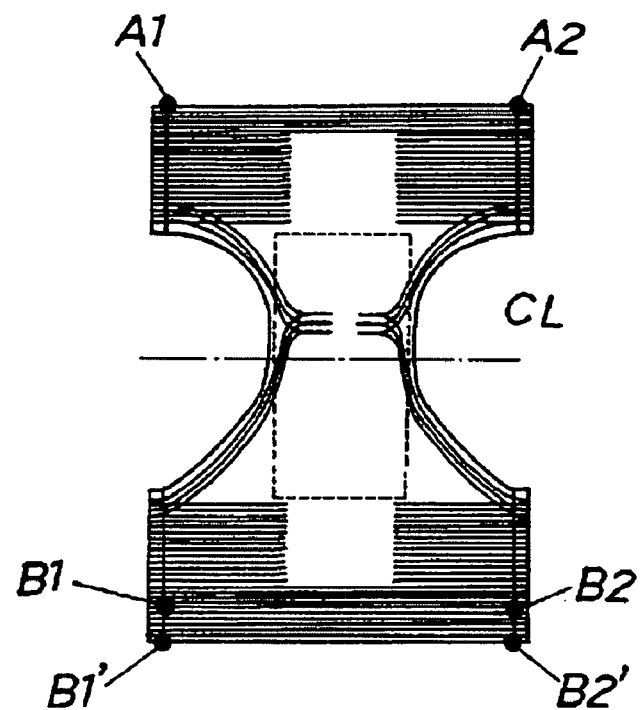
FIG. 10(b) is a plan of the diaper of FIG. 10(a) in its flat-out state.

Unlike that, there is a case where, as shown in FIGS. 10(a) and 10(b), the position of the upper edge of the waist opening portion on the stomach side is out of alignment with that on the back side, more specifically where the side edges A1 and A2 of the stomach portion A are not connected with side edges B1' and B2' of the back portion B but with side edges B1 and B2 of which the upper ends are positioned lower than those of the side edges B1' and B2', respectively. In that case, the centerline C is drawn in the same manner as described above, except that the band defined by the upper ends of the side edges B1' and B2' and the upper ends of the side edges B1 and B2 is assumed not to exist.

The whole length L (see FIG. 6) of the exterior laminate 10 in its flat-out state is freely selected. Nevertheless, L of the diaper 1 designed for children is preferably 470 to 540 mm taking into consideration a neat appearance both before and after a discharge and prevention of sliding down. For assuring a sense of security while worn, it is desirable for the diaper to completely cover the navel. From this viewpoint, L is more preferably 490 to 580 mm. L of the diaper 1 designed for adults is preferably 780 to 830 mm and, to completely cover the navel, more preferably 800 to 880 mm.

As stated previously, the diaper 1 according to the present embodiment is secured to the wearer's body by the constrictive force that primarily rests on the first elastic members 91a disposed in the first regions 91. In other words, the constrictive force of the elastic members disposed in the waist opening portion 7 is not a primary means for securing the diaper 1 to the body unlike the conventional pull-on diapers. On the contrary, an increased constrictive force of the waist opening portion 7 helps the diaper 1 to move down, which has been confirmed by the present inventors. From this point of view, the pressure imposed by the waist opening portion 7 of the diaper 1 of the present embodiment while worn is in the range of from 0.3 to 1.2 kPa, which range is lower than that employed in conventional pull-on diapers. It is preferred that the pressure of the waist opening portion 7 be lower than the average pressure of the first regions 91 by 0.5 to 1.0 kPa. The waist opening portion 7 which has its constrictive pressure falling within the recited range offers another advantage that the waist opening portion 7 is easy to widen, which makes diapering easy. If the pressure of the waist opening portion 7 is less than 0.3 kPa, the natural length of the diaper 1 before being worn may be so long that the diaper can have a poor appearance as a sort of a garment.

To ensure that the diaper 1 is kept in place more effectively, the pressure of the waist opening portion 7 is more preferably 0.4 to 1.0 kPa, even more preferably 0.4 to 0.8 kPa. The pressure of the waist opening portion 7 is measured in the same manner as used to measure the pressure of the first regions 91. That is, a 500 mm circumference cylinder is put in the diaper through the waist opening. An air pack of a clothing pressure measuring device is placed with its center positioned 15 mm below the waist opening edge to measure the wearing pressure. The measurement is conducted at 10 points at a 50 mm interval along the circumference. The average of the ten measurements is taken as a pressure of the waist opening portion.

Where the waist opening edge of the stomach side and that of the back side are not aligned as shown in FIGS. 10(a) and 10(b), the position nearest to the waist opening edge in the overlap of the stomach and the back portions is taken as the waist opening edge. The pressure exerted by the waist opening portion 7 is adjustable by, for example, selecting the material, thickness, elongation, and the spacing of the waist elastic members 71. Where the pressure by the waist opening portion 7 is in the range of the pressure by the first region 91, the position of the measurement is included in the first region 91. In the case of diapers for adults, a cylinder with circumference 850 mm is used in place of the cylinder with circumference 500 mm.

The pressure exerted by the diaper 1 of the present embodiment in its region except the first regions 91, the waist opening portion 7, and the leg opening portions 6, for example, the pressure by the second regions 92 located between the first regions 91 and the leg opening portions 6 is preferably 0.2 to 0.8 kPa, more preferably 0.3 to 0.6 kPa. With such a pressure design, the diaper 1 is kept in close and comfortable contact with the wearer's body, thus effectively preventing liquid leakage. The second regions 92 are applied to the body part below the iliac region, namely the lower abdominal region when the diaper 1 is worn. The second region 92 preferably has a width W2 (measured in the diaper length direction, see FIG. 6) of 40 to 70 mm, more preferably 45 to 65 mm.

Comparing the pressure values of the waist opening portion 7, the first regions 91, and the second regions 92 of the diaper 1 while worn, it is preferred that the pressure of the first region 91 be the highest, that of the waist opening portion 7 be the next highest, and that of the second region 92 be the lowest. The diaper 1 with such an order of wearing pressure values among the portions succeeds in keeping itself in place with a snug and comfortable fit against the wearer's body while worn thereby providing effective protection against leakage.

When designed for use by children, the diaper 1 of the present embodiment preferably has, in its flat-out state, a distance K3 (see FIG. 3(a)) of 30 to 55 mm, more preferably 35 to 50 mm, the distance K3 being defined from each side edge 41a of the central absorbent member 41 to the outboard edge 42a of each side absorbent member 42. The ratio of the distance K1 (see FIG. 6) to the distance K3 (i.e., K1/K3) and the ratio of the distance K2 (see FIG. 6) to the distance K3 (i.e., K2/K3) are each preferably 3.3 to 7.7, more preferably 4.0 to 6.6.

When designed for wear by adults, the diaper 1 of the present embodiment preferably has, in its flat-out state, a distance K3 (see FIG. 3(a)) of 50 to 80 mm, more preferably 55 to 75 mm, the distance K3 being defined from each side edge 41a of the central absorbent member 41 to the outboard edge 42a of each side absorbent member 42. The ratio of the distance K1 (see FIG. 6) to the distance K3 (i.e., K1/K3) and the ratio of the distance K2 (see FIG. 6) to the distance K3 (i.e., K2/K3) are each preferably 3.5 to 7.0, more preferably 4.0 to 6.4.

Figure 11:
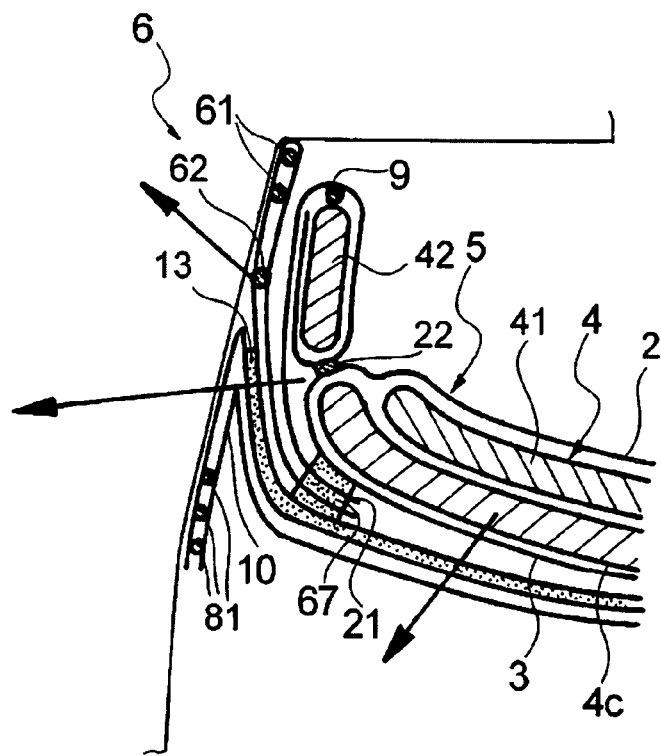
FIG. 11 is a half cross-section of the first embodiment of the diaper according to the first aspect of the invention while worn.

When all the distances K1, K2, and K3 satisfy the respective preferred ranges recited above, the risen side absorbent members 42 fit snugly into the wearer's groins while worn without twisting or gapping away from the skin in the crotch portion, as shown in FIG. 11. Thus, sagging or drooping of the crotch portion due to the presence of the side absorbent members 42 is prevented effectively, whereby sliding of the diaper can be prevented.

When K1/K3 and K2/K3 are each 7.7 or smaller, the gathers of the side absorbent members are easily allowed to fit into the groins, helping the diaper to provide a good fit. Furthermore, the diaper can be put on a wearer to provide a condition kept from sliding on the body by the first regions 91, whereby the diaper is prevented from sagging to provide an improved appearance.

When K1/K3 and K2/K3 are each 3.3 or greater, the side absorbent members are prevented from twisting in the crotch portion or, in dimensional relation to the first regions 91, prevented from making the crotch portion baggy, thereby providing a neat and natty diaper appearance.

Dividing the crotch region of an absorbent core 4 into a central absorbent member 41 and side absorbent members 42 that are located on both sides of the central absorbent member 41 and are configured to rise while worn is known as a means for improving leak protection. However, the present inventors found that such a configuration of conventional diapers increases a tendency of a diaper to slide down. The inventors also found that satisfying the preferred conditions of the distances K1, K2, and K3 provides prevention of such an increase of the sliding tendency and prevention of sagging of the crotch portion due to the weight of urine absorbed. When the diaper 1 satisfies the recited conditions of the distances K1, K2, and K3, an increase of the sliding tendency due to the presence of the side absorbent members 42 and sagging of the crotch portion due to the weight of urine are both prevented effectively.

To further enhance the prevention of an increase of the sliding tendency due to the presence of the side absorbent members 42 and the prevention of sagging of the crotch portion due to the weight of urine, the distance K3 is more preferably 35 to 50 mm, even more preferably 35 to 45 mm, and K1/K3 and K2/K3 are each more preferably 3.6 to 6.6, even more preferably 4.0 to 6.6.

For diapers for adults, K3 is more preferably 55 to 75 mm, even more preferably 60 to 70 mm, and K1/K3 and K2/K3 are each more preferably 4.0 to 6.4, even more preferably 4.3 to 5.8.

The distance K3 is measured on the centerline CL of the diaper.

To further enhance the prevention of an increase of the sliding tendency due to the presence of the side absorbent members 42, the central absorbent member 41 preferably has a width W (see FIG. 3(a)), measured on the centerline CL of the diaper, of 35 to 55 mm, more preferably 40 to 50 mm, for use by children and of 45 to 65 mm, more preferably 50 to 60 mm, for diapers for adults.

The ratio of the distance K3 to the width W, i.e., K3/W, is preferably 0.6 to 1.4, more preferably 0.7 to 1.1. The width of the absorbent core 4 on the centerline CL, i.e., K3×2+W, is preferably 100 to 150 mm, more preferably 100 to 140 mm, for diapers for children and preferably 190 to 220 mm, more preferably 190 to 210 mm, for diapers for adults.

In order that the risen side absorbent members 42 may have their distal outboard edges fit well in the wearer's groins over a considerable span in its longitudinal direction thereby to enhance the prevention of an increase of the sliding tendency, it is preferred that the gap 43 between the central absorbent member 41 and each side absorbent member 42 in the crotch portion C be widest in about the longitudinally middle part of the absorbent core 4 and be gradually tapered to the longitudinal ends thereof as shown in FIG. 3(a).

The shape of each gap 43 is more preferably one defined by the inboard edge of each side absorbent member 42 which is straight and a side edge of the central absorbent member 41 which is straight or slightly arcuately curved in its longitudinally middle part and gradually approaching to the straight inboard edge of the side absorbent member 42 in directions to its longitudinally ends as shown in FIG. 3(a). Each side absorbent member 42 preferably has a length L1 (see FIG. 3(a)) of 170 to 220 mm, more preferably 175 to 210 mm.

Members constituting the diaper 1 of the present embodiment can be made of any materials that have commonly been used in the art with no particular limitation. For example, hydrophilic and liquid permeable nonwoven fabric or a perforated film can be used as the topsheet 2, and a water impermeable or water repellent material can be used as the backsheet 3. Examples of the water impermeable material include a resin film and a laminate of resin film and nonwoven fabric. Examples of the water repellent material include water repellent nonwoven fabric. The same nonwoven fabrics as described below for use as cuff-forming sheets can be used as the water repellent nonwoven fabrics.

The absorbent core 4 can be formed of, e.g., a fiber aggregate made of pulp fiber or continuous fiber (tow) or a mixture of such a fiber aggregate and a superabsorbent polymer (superabsorbent polymer/fiber material mixed airlaid layer). Examples of the superabsorbent polymer include sodium polyacrylate, an acrylic acid/vinyl alcohol copolymer, crosslinked sodium polyacrylate, a starch/acrylic acid graft copolymer, an isobutylene/maleic anhydride copolymer and a saponification product thereof, and polyaspartic acid. Examples of the fibers making up the absorbent core 4 include hydrophilic fibers such as pulp fiber, rayon fiber, cotton fiber, and cellulose acetate; polyolefin fibers such as polyethylene and polypropylene; polyester fibers; and condensed resin fibers such as polyamide. The superabsorbent polymers may be used either individually or as a combination of two or more thereof, and so may be the fibers.

Sheet materials that can be used as the cuff-forming sheet 60 include multi-layered composite nonwoven fabrics such as spun bonded/melt blown/spun bonded nonwoven, spun bonded nonwoven, heat bonded nonwoven, and air-through nonwoven. Multi-layered composite nonwoven composed of spun bonded and melt blown is preferred in terms of flexibility and water resistance. The cuff-forming sheet 60 preferably has a basis weight of about 12 g/m$^2$.

The cuff-forming sheet preferably has a water pressure resistance of 3 cm or more, more preferably 5 cm or more, as measured in accordance with the water resistance test method (low water pressure method) specified in JIS L1092:1998, "testing methods for water resistance of textiles". In measuring the water pressure resistance, a water level gauge containing water is elevated at a rate of 10±0.5 cm/min, and the water level is read at which appearance of water drops at three places on the reverse side of the test piece is observed with the naked eye. The measurement should be taken without delay after completion of clamping the test piece.

According to the present embodiment, the diaper 1 has its first regions 91 snugly applied to the wearer's iliac region and is thereby effectively prevented from sliding down. Furthermore, the diaper's own tendency to slide down is hardly urged by the risen side absorbent members 42. Therefore, the diaper hardly slides or slips downward due to the movement of the wearer during use, keeps an aesthetic appearance while worn, and causes no interference with the wearer's movement.

Since diaper's sliding is effectively prevented without relying on the waist elastic members, the wearer's body is protected from encountering too strong constrictive force by the elastic members disposed in the diaper so that a wearing comfort is provided. Prevention of the diaper's sliding provides further ensured protection against leakage of urine and feces during use.

Figure 12A:
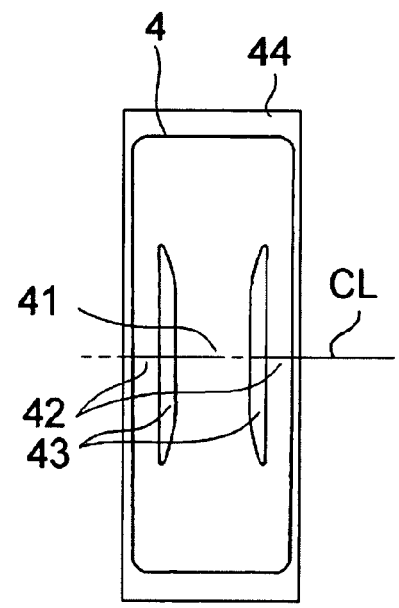
FIG. 12(a) is a plan of an absorbent core used in another embodiment of the diaper according to the first aspect of the invention.
Figure 12B:
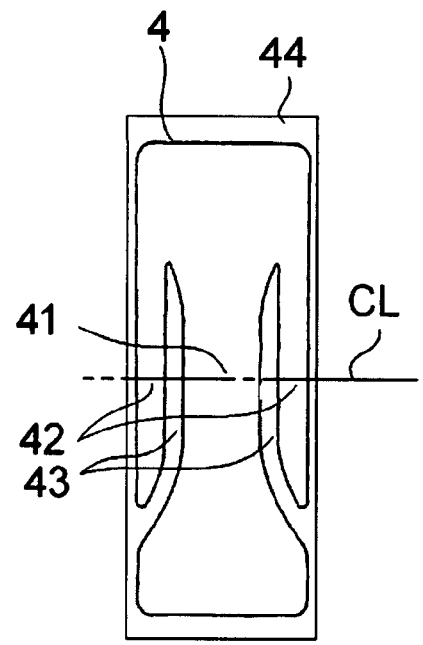
FIG. 12(b) is a plan of an absorbent core used in still another embodiment of the diaper according to the first aspect of the invention.
Figure 12C:
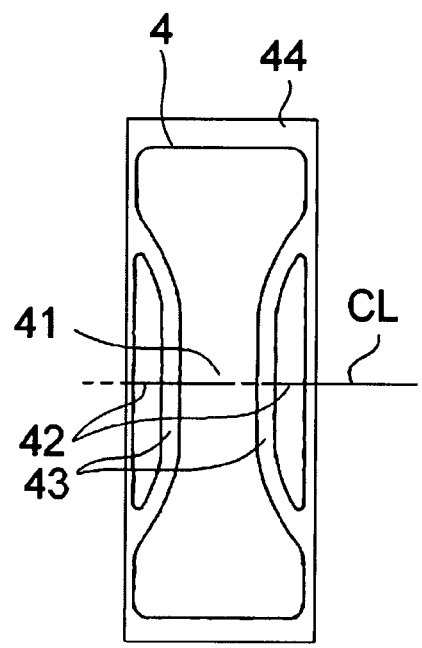
FIG. 12(c) is a plan of an absorbent core used in yet another embodiment of the diaper according to the first aspect of the invention.
Figure 13:
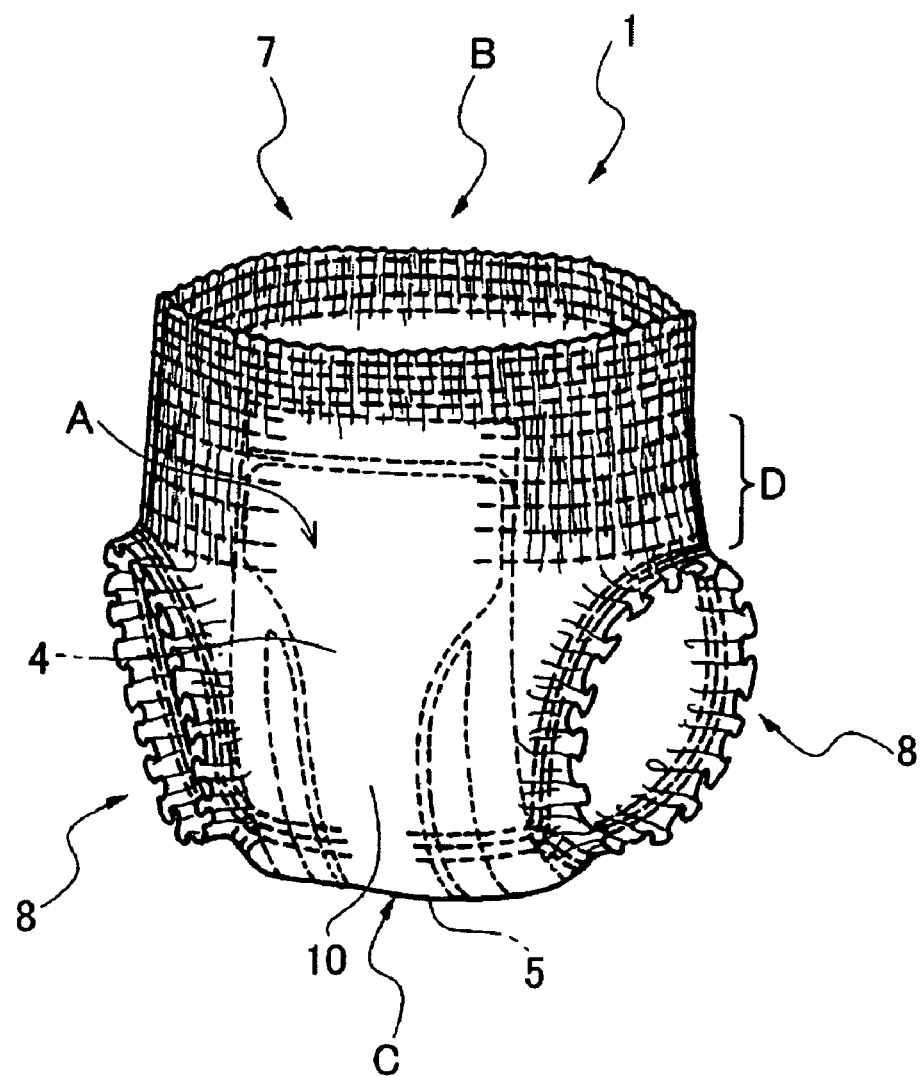
FIG. 13 is a perspective of a preferred embodiment (second embodiment) of a pull-on disposable diaper according to the second aspect of the present invention.

While the first aspect of the present invention has been described based on its preferred embodiment, the first aspect of the invention is not limited to the above embodiment. For instance, the absorbent core may have any of the configurations shown in FIGS. 12(a) to 12(c). In FIGS. 12(a) to 12(c), numeral 44 indicates tissue paper wrapping the absorbent core 41, and the portion that covers the skin facing side of the absorbent core 4 is taken away. While the absorbent cores 4 shown in FIGS. 12(a) to 12(c) do not have a multi-layered structure near the point of discharge, the central absorbent member 41 of these absorbent cores 4 may have a multi-layered structure including a dual layer structure as in the diaper 1 described supra.

The absorbent core 4 of FIG. 12(a) is formed of a single layer absorbent member having the central absorbent member 41 and the pair of side absorbent members 42 integral with each other. In the absorbent core 4 of FIG. 12(b), the pair of side absorbent members 42 is continuous to one longitudinal end portion of the central absorbent member 41 but discontinuous to the opposite end portion. That is, each gap 43 is open at one longitudinal end thereof. The absorbent core 4 of FIG. 12(c) has the pair of side absorbent members 42 separated from the central absorbent member 41 so that each gap 43 is open at both longitudinal ends thereof.

The diaper 1 has the lateral side edges A1 and A2 of the stomach portion A and the lateral side edges B1 and B2 of the back portion B that are connected by sealing to form a pair of side seams S. Alternatively, they may be connected by means of various fastening means, such as snap fasteners, buttons, and hook and loop fasteners. The positions of the side seams or the positions of connecting the lateral sides edges A1 and B1 and the lateral side edges A2 and B2 do not need to be right on the sides of a wearer's body and may be slightly off the sides to the stomach side or the back side. While the exterior laminate 10 used in the above embodiment is composed of the outer nonwoven fabric sheet 11 and the inner nonwoven fabric sheet 12, the exterior laminate is not limited to these materials and, for example, may be a laminate of a nonwoven fabric sheet and a water repellent sheet.

The second aspect of the present invention is then described based on its preferred embodiment (second embodiment of the invention) by way of the accompanying drawing.

The disposable diaper 1 (hereinafter also referred simply to as "diaper 1") of the second embodiment is a so-called pull-on diaper. As shown in FIGS. 13, 14, 15(a) to 15(c), 4, and 5, the diaper 1 includes an absorbent body 5 and an exterior laminate 10 on the garment-facing side of the absorbent body 5. The absorbent body 5 has a liquid permeable topsheet 2 and a liquid retentive absorbent core 4.

The diaper of the second embodiment has the same cross-sectional structure as the diaper of the first embodiment so that FIGS. 4 and 5, which are cross-sections of the diaper of the first embodiment, will be referred to in describing the second embodiment.

The diaper 1 of the second embodiment is sectioned into a stomach portion A applied to the stomach side of a wearer, a back portion B applied to the back side of a wearer, and a crotch portion C positioned between the portions A and B while worn. The stomach portion A, back portion B, and crotch portion C of the diaper 1 corresponds to approximately equal trisections along the longitudinal direction of the diaper 1 in its flat-out state shown in FIG. 14 with every elastic member stretched out.

As used herein, the term "garment facing side" denotes the opposite side of each member, such as an absorbent body, to the side that is to be directed to the skin of a wearer. The term "skin facing side" means the side of each member that is to face the skin of a wearer.

The term "longitudinal direction" as used herein refers to a direction parallel with a long side of each member. The term "lateral (or width) direction" refers to a direction perpendicular to the longitudinal direction.

The absorbent body 5 has an oblong rectangular shape. It is bonded to a laterally middle portion of the exterior laminate 10 with its longitudinal direction coinciding with the longitudinal direction of the diaper to straddle the stomach portion A and the back portion B by means of known bonding means such as a hot-melt adhesive.

The exterior laminate 10 is joined to itself along both side edges of the stomach portion A and both side edges of the back portion B by any known joining means such as heat sealing, high frequency sealing or ultrasonic sealing, thereby forming a pair of side seams, a waist opening portion 7, and a pair of leg opening portions 8.

The aforementioned structure of the diaper 1 is the same as that of conventionally known diapers.

Figure 14:
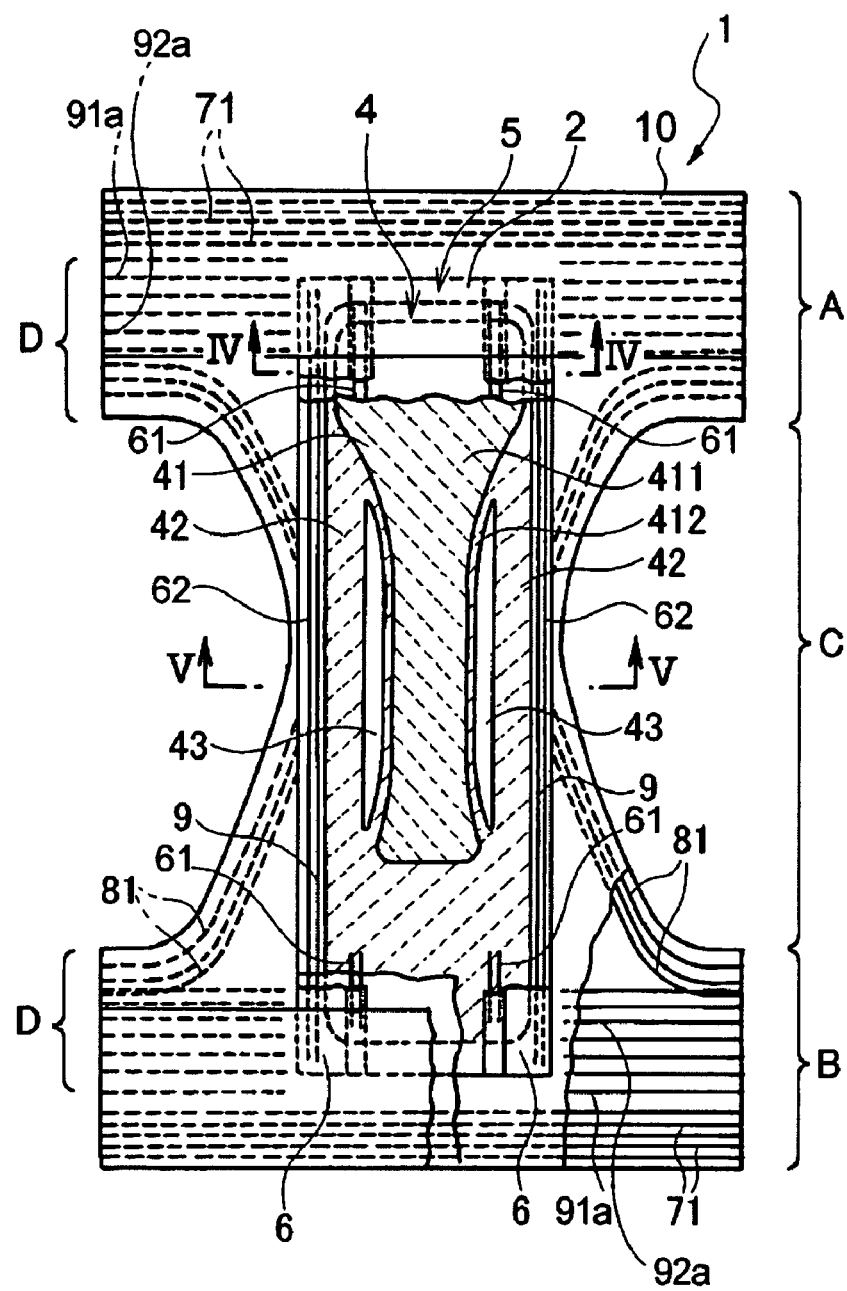
FIG. 14 is a plan of the diaper of FIG. 13 in its flat-out state, with the side seams cut open, every elastic member stretched out, and a part cut away.

The diaper 1 of the second embodiment has a pair of elastic members 9 for raising both side portions of the absorbent body 5 (specifically side absorbent members 42 hereinafter described) disposed along the entire length of the long side edges of the absorbent core 4 as shown in FIG. 14. Thus, the absorbent body 5 is configured to raise both of its side portions 52 in the crotch portion C (the side absorbent members 42) as shown in FIG. 5.

A pair of leak-preventive cuffs 6 are provided on both sides of the absorbent body 5. Each cuff 6 includes a cuff-forming sheet 60 joined to the absorbent body 5, cuff-forming elastic members 61 fixed in their extended state to near the free edge of the cuff-forming sheet 60, and an elastic member (intermediate elastic member) 62 for drawing the cuff up and inward (hereinafter referred to as a cuff-drawing elastic member 62). The cuff-drawing elastic member 62 is fixed in its stretched state to a position intermediate the free edge and the fixed edge of the cuff 6.

The absorbent core 4 has a generally oblong rectangular shape (80 to 170 mm wide and 300 to 500 mm long) lying along the longitudinal direction of the diaper 1 in a plan view as shown in FIGS. 13,14, and 15(a) to 15(c). It is totally wrapped in a water permeable cover sheet (not shown) formed of tissue paper or water permeable nonwoven fabric.

The absorbent core 4 includes a sand glass-shaped central absorbent member 41 and a pair of side absorbent members 42 disposed on both sides of the central absorbent member 41 in a symmetrical configuration. The central absorbent member 41 is discrete from the side absorbent members 42 in at least the crotch portion C. One longitudinal end portion and the other longitudinal end portion of each side absorbent member 42 are continuous with one longitudinal end portion (stomach portion) F and the other longitudinal end portion (back portion) R, respectively, of the central absorbent member 41. Accordingly, a closed gap 43 is formed between the central absorbent member 41 and each of the pair of side absorbent members 42.

The one longitudinal end portion F (hereinafter "front portion F"), a longitudinally middle portion M (hereinafter "middle portion M"), and the other longitudinal end portion R (hereinafter "rear portion R") of the absorbent core 4 correspond to approximately one-third of the length of the absorbent core 4 shown in FIG. 15(a).

As shown in 14, the absorbent core 4 is configured such that the side absorbent members 42 may be disposed in at least the crotch portion C of the diaper 1. In addition to this, the absorbent core 4 is configured such that front portion F of the central absorbent member 41 may be located in the stomach portion A of the diaper 1.

The central absorbent member 41 is composed of a T-shaped upper absorbent submember 411 and a sandglass-shaped lower absorbent submember 412 larger than the upper absorbent submember 411. The upper absorbent submember 411 is superposed on the skin facing side of the lower absorbent submember in a region straddling the front portion F and the middle portion M (i.e., near the point of urination). The pair of side absorbent members 42 are integral with the lower absorbent submember 412. The part of the lower absorbent submember 412 that sticks out from the edge of the upper absorbent submember 411 preferably has a width d (see FIG. 15(a)) of 0 to 20 mm, more preferably 5 to 15 mm.

According to disposing the lower absorbent submember 412 and the upper absorbent submember 411 near the point of urination in a superposed relation as described, the substantial amount of the superabsorbent polymer and pulp is increased in the vicinity of the urination point without involving a considerable increase of the total diaper thickness. This leads to improvement of use efficiency of the absorbent polymer and pulp and achievement of a superior protection against leakage.

The basis weight of polymer of the upper absorbent submember 411 is preferably 80 to 230 $g/m^2$, more preferably 100 to 200 $g/m^2$, and the basis weight of pulp is 80 to 230 $g/m^2$, more preferably 100 to 200 $g/m^2$. The lower absorbent submember 412 preferably has the same basis weight ranges of the polymer and pulp as the upper absorbent submember 411.

If the basis weights of the polymer and the pulp of the upper absorbent submember 411 and the lower absorbent submember 412 are less than the respective lower limits recited above, the leak prevention tends to be insufficient, or formation of the these submembers tends to be unstable (difficulty tends to be encountered in uniformly distributing the polymer or pulp). If the basis weights of the polymer and the pulp of the upper absorbent submember 411 and the lower absorbent submember 412 are more than the respective upper limits recited, the absorbent core tends to provide a poor fit or puff out and become baggy in the crotch portion after urination to cause discomfort to the wearer.

Both the upper absorbent submember 411 and the lower absorbent submember 412 preferably have a polymer to pulp weight ratio of 4:6 to 6:4 taking mixing uniformity into consideration. Taking into consideration the appearance of the crotch portion after urine absorption (prevention of a baggy appearance due to swell of the polymer), the total basis weight of the polymer in the upper absorbent submember 411 and that in the lower absorbent submember 412 is preferably 160 to 400 $g/m^2$.

Figure 15A:
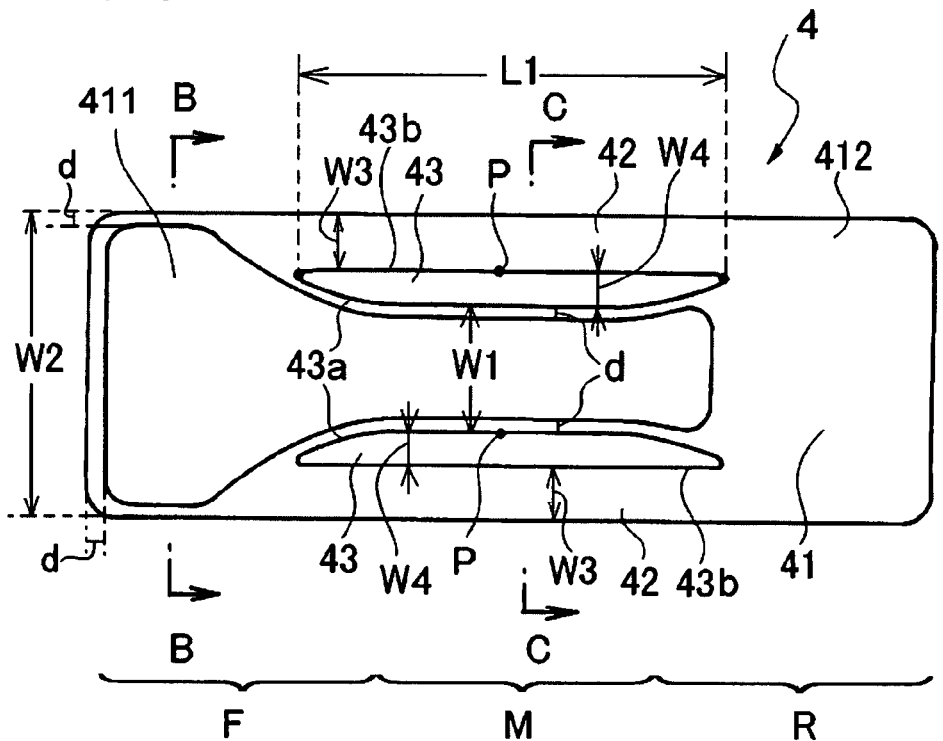
FIG. 15(a) is a plan of an absorbent core used in the diaper of FIG. 13.
Figure 15B:
FIG. 15(b) is a cross-section taken along line B-B in FIG. 15(a).
Figure 15C:
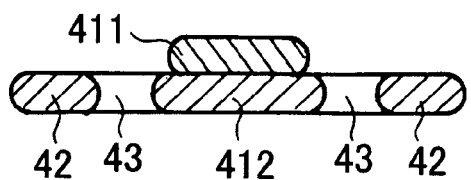
FIG. 15(c) is a cross-section taken along line C-C in FIG. 15(a).

The width W1 (see FIG. 15(a)) of the central absorbent member 41 in the middle portion M, that is, the width W1 of the lower absorbent submember 412 in the middle portion M, is preferably 30 to 80 mm, more preferably 40 to 70 mm. The middle portion M of the central absorbent member 412 is the region that is located in the crotch portion C. If the width W1 in the middle portion M is smaller than 30 mm, leakage can occur easily particularly in the crotch portion, and the processability during the making of the central absorbent member 41 tends to be poor. If the width W1 exceeds 80 mm, the diaper tends to provide a poor appearance and fit in the crotch portion during wear.

The absorbent core 4 inclusive of the lower absorbent submember 412 and the pair of side absorbent members 42 preferably has a width W2 (see FIG. 15(a)) of 80 to 170 mm, more preferably 90 to 160 mm, to secure a neat appearance during wear and a good fit in the crotch portion.

The side absorbent member 42 preferably has a length L1 (the dimension in the diaper's longitudinal direction, see FIG. 15(a)) of 100 to 270 mm, more preferably 120 to 250 mm, and a width W3 (see FIG. 15(a)) of 10 to 50 mm, more preferably 15 to 45 mm.

The widths W1, W2, and W3 are values measured on the transverse centerline that divides the length of the central absorbent member 41 into equal halves.

The gap 43 has a bowed shape extending longitudinally of the absorbent core 4 as shown in FIG. 15(a). The length of the gap 43 coincides with the length L1 of the side absorbent member 42. The gap 43 preferably has a width W4 (see FIG. 15(a)) of 5 to 30 mm, more preferably 5 to 25 mm.

In detail, the gap 43 is defined by an outboard border 43b and an inboard border 43a. The outboard border 43b is a straight line that extends along the inboard edge of the side absorbent member 42. The inboard border 43a is a curved line that extends along the outboard edge of the central absorbent member 41. It is preferred that the curve of the inboard border 43a be macroscopically the same as the curve of the groin of a wearer.

The term "straight line" as used above means not only a geometrically defined straight line but a slightly curved or distorted and yet macroscopically straight line. The term "curved line" as used above means not only a curve that curves in one direction and contains no straight segment but a macroscopically curved line, such as a curve that partly curves in an opposite direction or a curve containing a straight segment. In the present embodiment, the longitudinally middle part of the inboard border 43a of the gap 43 is straight.

In the second embodiment, the topsheet 2 of the diaper 1 covers the entire area of the skin facing side 4a of the absorbent core 4, the entire area of both side edge faces 4b of the absorbent core 4, and both side portions and their vicinity of the garment facing side 4c of the absorbent core 4 as shown in FIGS. 4 and 5. Both side edge portions 21 of the topsheet 2 cover part of the garment facing side of the central absorbent member 41 in the second embodiment.

In the second embodiment, the absorbent body 5 of the diaper 1 has a liquid impermeable backsheet 3 that covers the entire area of the garment facing side 4c of the absorbent core 4 as shown in FIGS. 4 and 5. The backsheet 3 is fixedly held between the absorbent core 4 and the portions of the topsheet 2 that cover the side portions and their vicinities of the garment facing side 4c of the absorbent core 4.

The term "entire area" used herein includes a substantially entire area. Specifically, when the backsheet 3 covers an area including at least 90% of the width and at least 90% of the length of the garment facing side 4c of the absorbent core 4c, the backsheet 3 is regarded as covering the entire area of the garment facing side 4c of the absorbent core 4. When the backsheet 3 has a larger width and/or length than the width (W2 in FIG. 15(a)) and/or length of the absorbent core 4, it is preferred that the width of the backsheet 3 be 110% or less of the width of the absorbent core 4 and, likewise, the length of the backsheet 3 be 110% or more of the length of the absorbent core 4.

In the case where the absorbent core 4 is wrapped in a water permeable cover sheet, the width and length of the absorbent core 4 are those inclusive of the cover sheet.

The topsheet 2 is fixedly joined in both of its side edge portions 21 to the backsheet 3 and the cuff-forming sheets 60 by joining means such as heat sealing to form an absorbent body joints 67.

Each absorbent body joint 67 is located inward of the most inner side position P of the inboard edge of each side absorbent member 42 as shown in FIG. 5. The pair of elastic members 9 for raising the side portions of the absorbent body 5 (the side absorbent members 42) (hereinafter referred to as side absorbent member-raising elastic members 9) are disposed in their stretched state outboard of the absorbent body joints 67. With respect to the position of the absorbent body joint 67, the position of the distal outboard edge of the joint 67 is referred to.

The absorbent body joints 67 are formed by joining the cuff-forming sheets 60, the side edge portions 21 of the topsheet 2, and the backsheet 3 by known joining means such as heat sealing, high frequency sealing, ultrasonic sealing or application of a hot-melt adhesive. While in the second embodiment the absorbent body joints 67 have a continuous straight linear shape, the shape of the absorbent body joins 67 is not limited thereto and may be, for example, a discontinuous straight line (a straight line broken up by gaps) or a continuous or discontinuous curve.

The topsheet 2 covering the skin facing side 4a of the absorbent core 4 and the backsheet 3 covering the garment facing side 4c of the absorbent core 4 are joined to each other in the gaps 43 of the absorbent core 4 in the crotch portion to form topsheet/backsheet joints 22 as shown in FIG. 5. Since the gaps 43 are covered with the cover sheet (not shown) as stated above, the topsheet 2 and the backsheet 3 are bonded to each other via the cover sheet.

To the skin facing side of the exterior laminate 10 are bonded the cuff-forming sheets 60 and the absorbent body 5 in that order. The cuff-forming sheets 60 are bonded to the exterior laminate 10 via a joint (hereinafter also referred to as an exterior laminate joint) 13. The outboard edges of the exterior laminate joint 13 are outboard of the absorbent body joints 67. The distance L5 (see FIG. 5) between the outboard edge of the exterior laminate joint 13 and the outboard edge of the absorbent body joint 67 is preferably 0 to 50 mm, more preferably 10 to 40 mm. The bonding of these members is effected by, for example, application of a hot melt adhesive.

The exterior laminate 10 has two exterior laminate-forming sheets 11 and 12 and elastic members fixed therebetween at the respective places as shown in FIGS. 14, 4 and 5. Between the two exterior laminate-forming sheets 11 and 12 are fixed waist elastic members 71 that gather the waist opening portion 7 to form waist gather, leg elastic members 81 that gather the leg opening portions 8 to form leg gather, and below-waist elastic members 91a and 92a that form below-waist gather all in their stretched state by bonding means such as a hot melt adhesive. The below-waist elastic members 91a and 92a are disposed in a below-waist portion D defined to be a region between 20 mm below the upper edge of the waist opening portion 7 and the upper ends of the leg opening portions 8) and divided into left and right parts.

The exterior laminate-forming sheets 11 and 12 are each formed of breathable nonwoven fabric. The garment facing one of the two sheets (outer nonwoven sheet 11) extends outward from the front and rear ends (both longitudinal ends) of the skin facing one (inner nonwoven sheet 12). With the absorbent body 5 placed on the sheet 12 of the exterior laminate 10, the extensions are folded back to cover the front and rear portions of the absorbent body 5 and bonded thereto.

As shown in FIGS. 14, 4, and 5, the pair of cuffs 6 are provided on both sides of the absorbent body 5. Each cuff 6 extends in the diaper's longitudinal direction. Each cuff 6 includes a cuff-forming sheet 60, a plurality of cuff-forming elastic members 61, and one cuff-drawing elastic member 62.

In the diaper 1 of the second embodiment, a dual layer sheet is used as a cuff-forming sheet 60. The dual layer sheet is formed by folding a water repellent strip of prescribed width in two along a longitudinal folding line and joining the facing two panels with a hot-melt adhesive or partial heat sealing or ultrasonic sealing, etc.

The cuff-forming elastic members 61 and the cuff-drawing elastic member 62 are fixed in their stretched state between the facing panels of each cuff-forming sheet 60.

As shown in FIG. 4, the cuff-forming sheets 60 cover both the side portions of the absorbent body 5 straddling the skin facing side and the garment facing side in each of the stomach portion A and the back portion B, more specifically in both longitudinal end portions of the absorbent body 5. The cuff-forming sheets 60 are bonded to the skin facing side of the absorbent body 5 at the longitudinal end portions of the absorbent body 5 by known bonding means such as heat sealing, high frequency sealing, ultrasonic sealing or application of a hot melt adhesive.

As shown in FIG. 5, the cuffs 6 are capable of rising in at least the crotch portion C. The plurality of cuff-forming elastic members 61 are arranged in parallel in the width direction of the absorbent body 5 near the free edge (folded edge of the cuff-forming sheet 60) of each cuff 6 over the whole length of the cuff-forming sheet 60 (cuff 6). So arranged, the distal part of the risen cuff 6 comes into planar contact with the wearer's skin. As a result, the contact of the diaper with the body is tight to provide improved leakage protection and yet soft feel of touch.

The cuff-drawing elastic member 62 is disposed in the cuff 6 between the cuff-forming elastic members 61 and the absorbent body joint 67 along the whole length of the cuff-forming sheet 60 (cuff 6). The cuff-drawing elastic member 62 is positioned outboard of the side absorbent member-raising elastic member 9 in the leak-preventive cuff 6 in a flat-out state of the diaper 1.

In order to obtain hereinafter described effects of the second embodiment, it is preferred that the absorbent body joint 67, cuff-drawing elastic member 62, side absorbent member-raising elastic member 9, and cuff-forming elastic members 61 on each side of the diaper 1 be in the following positional relation in their flat-out state.

The distance L2 (see FIG. 4) between the outboard edge of the absorbent body joint 67 and the center of the cuff-drawing elastic member 62 is preferably 30 to 70 mm, more preferably 35 to 60 mm. In the case where two or more cuff-drawing elastic members 62 are provided on each side, the distance L2 is measured from the closest one of the elastic members 62 to the absorbent member joint 67.

The center-to-center distance L4 (see FIG. 4) between the cuff-drawing elastic member 62 and the cuff-forming elastic member 61 is preferably 20 to 50 mm, more preferably 20 to 40 mm. In the case where two or more cuff-drawing elastic members 62 are provided on each side, the distance L4 is measured from the closest one to the absorbent member joint 67. In the case where two or more cuff-forming elastic members 61 are provided as in the second embodiment, the distance L4 is measured from the most outboard one of them.

The fewer the number of the cuff-drawing elastic members 62, the better to prevent leaving a mark made by the elastic members around the wearer's thighs. The number of the elastic members is preferably one or two.

Members constituting the diaper 1 of the second embodiment can be made of any materials that have commonly been used in the art with no particular limitation similarly to the first embodiment.

The cuff-forming elastic members 61 and cuff-drawing elastic members 62 preferably have the shape of string or tape with a prescribed width. Elastic strings are particularly referred. Examples of the materials of the elastic members 61 and 62 include natural rubber, synthetic rubbers such as styrene-butadiene, butadiene, isoprene, and neoprene, EVA, extensible polyolefins, and urethane. The elastic members 9, 71, 81, 91a, and 92a may have the shape of string, tape with a prescribed width, film, etc. made of materials the examples of which have been recited above as a material of the elastic members 61 and 62.

Figure 16:
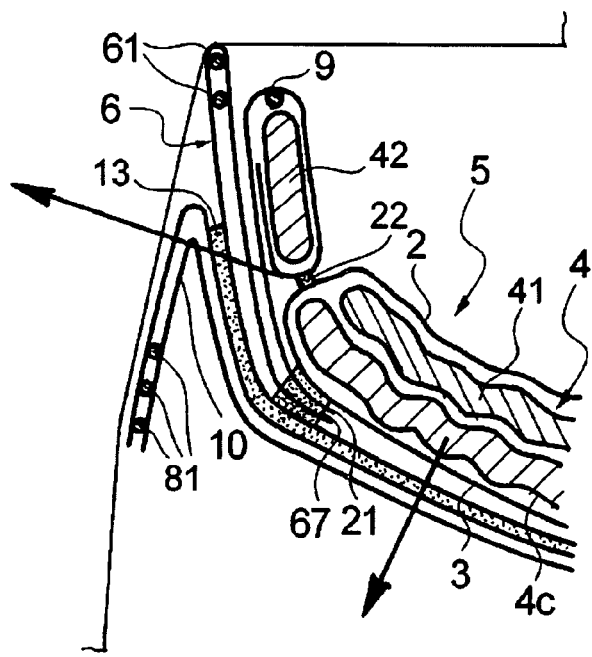
FIG. 16 is a half cross-section of a comparative and referential diaper relevant to the diaper according to the second aspect of the invention in its worn state.

According to the second embodiment, the diaper 1 has the following effects resulting from the provision of the cuff-drawing elastic members 62 separately from the cuff-forming elastic members 61. In FIG. 16 is shown a comparative referential form of the diaper 1 of the second embodiment with the cuff-drawing elastic member 62 taken away. Should the cuff-drawing elastic member 62 be absent, the force of the cuff 6 pulling the side absorbent member 42 to the wearer's thigh will be insufficient to stabilize the position of the foot where the side absorbent member 42 rises (the position of the inboard edge of the side absorbent member 42) as shown in FIG. 16. The force of pulling the central absorbent member 41 will also be so weak that the central absorbent member 41 will be compressed laterally inward and unstable in shape. It follows that the diaper hardly has a good fit and protection against leakage in the crotch portion.

In the diaper 1 of the second embodiment, in contrast, since the cuff-drawing elastic member 62 is provided in the cuff 6 as shown in FIG. 11, the region between the free edge of the cuff 6 where the cuff-forming elastic members 61 are disposed and the exterior laminate joint 13 (the joint between the cuff 6 and the exterior laminate 10) is pulled to the wearer's thigh by contraction. It follows that the side absorbent member 42, particularly the foot for rising, is pulled to the wearer's thigh via the topsheet 2 and easily applied to the inner thigh. Furthermore, the side absorbent member 42 being pulled to the thigh, the central absorbent member 41 is also pulled laterally outward and thereby stabilized in shape. As a result, the diaper will have a neat appearance and improved leakage protection in the crotch portion.

Although FIG. 11 is a cross-section of the diaper of the first embodiment, it has been and will be used to describe the second embodiment because of the similarity of the cross-sectional view between the first and second embodiments.

According to the second embodiment, the outboard edges of the exterior laminate joint 13 are positioned laterally outboard of the absorbent body joints 67. The exterior laminate 10 being pulled laterally outward by the contraction of the elastic members 81 disposed along the leg opening portion 8, the absorbent core 4 (including the side absorbent member 42 on each side and the central absorbent member 41) is also efficiently pulled laterally outward via the exterior laminate joint 13, the cuff-forming sheet 60, and the absorbent member joint 67. As a result, the appearance and leak protection in the crotch portion are further improved.

Since the cuff 6 is provided with the cuff-drawing elastic member 62, the elastic member 62 contracts to prevent the cuff 6 from hanging out of the leg opening portion 8 while worn.

Since the topsheet 2 covering the skin facing side 4a of the absorbent core 4 and the backsheet 3 covering the garment facing side 4c of the absorbent core 4 are joined to each other at the joints 22 formed in the gaps 43 of the absorbent core 4, the central absorbent member 41 hardly sags away from the topsheet 2 even with the rising of the side absorbent members 42.

Figure 17:
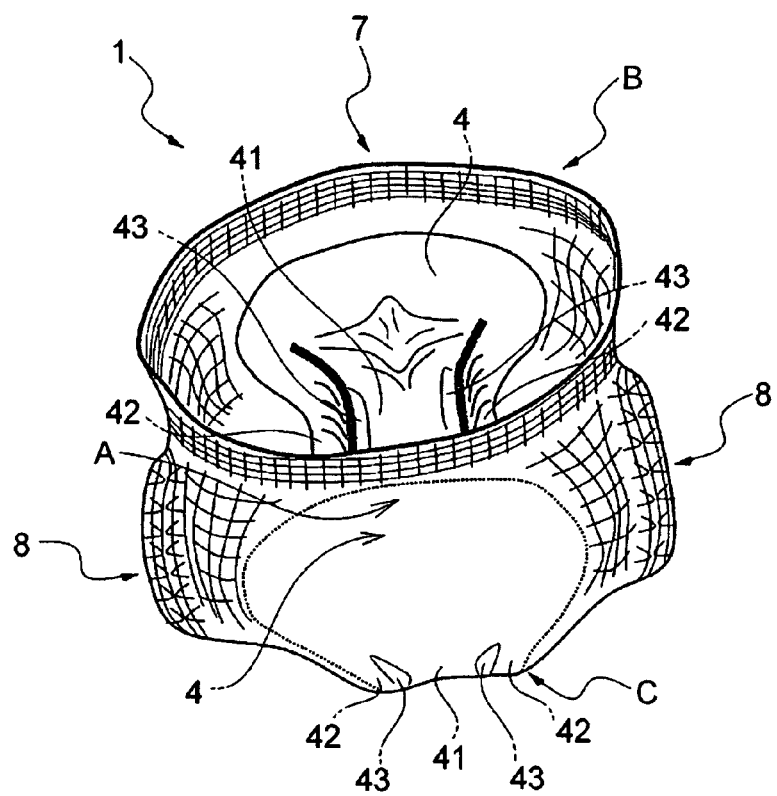
FIG. 17 is a schematic perspective of the diaper of the second embodiment while worn by a wearer in a sitting posture.

Since the front portion and the rear portion of each side absorbent member 42 connect to the front portion F and the rear portion R of the central absorbent member 41, respectively, the diaper 1 provides high protection against leakage of urine and feces particularly when a wearer is in a sitting posture. In some detail, when a wearer assumes a sitting posture, the risen side absorbent members 42 move to place themselves over the central absorbent member 41 to press the central absorbent member 41 forward and rearward, as shown in FIG. 17. As a result, the diaper 1 is puffed out to make a space which surrounds the discharge points of wastes of the wearer and is not collapsed even with the wearer being in a sitting posture. Therefore, urine or feces discharged by a sitting wearer is contained in the space and effectively prevented from leaking.

By virtue of the characteristic configuration of the absorbent core 4 as described, the diaper does not become baggy in its crotch portion and provides a neat appearance while worn, a snug fit of the crotch portion, and superior leakage protection. Because of the presence of the gaps 43 between the central absorbent member 41 and the side absorbent members 42, the side absorbent members 42 exhibit satisfactory rising capability even when they have high basis weights of pulp and polymer. Since the central absorbent member 41 and the pair of side absorbent members 42 are connected to each other, the absorbent core 4 is easy to handle in the manufacture of the diaper 1. The gaps 43 can be located in the diaper 1 as designed with high accuracy in a stable manner. Thus, the diaper 1 having excellent characteristics can be manufactured efficiently and stably.

Since the inboard border 43a of the gap 43 is laterally inwardly curved, the absorbent core 4 is pressed inwardly by the wearer's groins while worn, whereby the side absorbent members 42 rise along the edges of the central absorbent member 41 in the crotch portion C. Thus, the inboard border 43a easily coincides with the inner thigh of the wearer, and the diaper gives no discomfort to the wearer and provides a good protection against leakage.

The front portion F of the central absorbent member 41, which is disposed in the stomach portion A of the diaper, is composed of the upper absorbent submember 411 and the lower absorbent submember 412. In other words, the absorption capacity of the absorbent core is localized in the front (stomach) portion thereof. Therefore, the diaper is highly protective against leakage particularly from its front side. For use by children, for example, the diaper achieves a protection against leakage from its front side even when used by a child lying on its stomach.

The absorbent body joints 67 are located inboard of the most inboard points P of the side absorbent members 42, and the elastic members 9 for raising the respective long side portions (side absorbent members 42) of the absorbent body 5 are disposed outboard of the absorbent member joints 67. By this configuration, the side portions 52 of the absorbent body 5 and the cuffs 6 largely rise toward the wearer's body in the crotch portion C as shown in FIG. 5. The diaper exhibits improved anti-leakage performance as a result. This configuration makes the absorbent body 5 easily rise in the front, rear, and both side portions thereof to form a containment pocket in the crotch portion C, from which bodily discharges hardly leak. Even when a large quantity of urine is discharged at a time or even when less absorbable loose or watery stool is discharged, the discharges hardly leak from the pocket.

Even if some bodily wastes leak from the containment pocket, there are a pair of leak-preventive cuffs 6 on both sides of the absorbent body 5 to form a pair of pockets Q (see FIG. 5) providing excellent containment of wastes between the risen side portions 52 of the absorbent body 5 and the cuff-forming sheets 60. Therefore, the bodily wastes are prevented from leaking off the edge of the exterior laminate 10.

Since the cuffs 6 come into planar contact with the wearer's skin, and the risen side portions 52 of the absorbent body 5 hardly come into direct contact with the wearer's skin, the diaper gives little discomfort to the wearer.

The second aspect of the present invention will then be described based on third to fifth embodiments of the invention. The description about the second embodiment applies to the third to fifth embodiments, unless stated otherwise.

Figure 18:
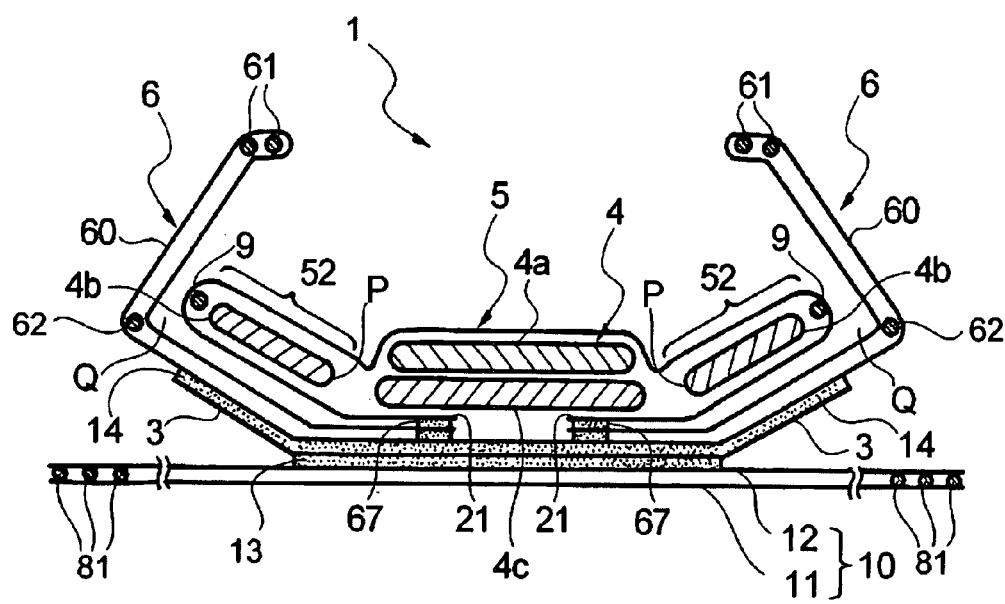
FIG. 18 is a cross-section of a third embodiment of the second aspect of the invention, which corresponds to FIG. 5.

FIG. 18 is a view corresponding to FIG. 5, illustrating a third embodiment of the present invention. The third embodiment is structurally the same as the second embodiment, except for the location of the backsheet 3 and the pattern of the joint between the backsheet 3 and the cuff-forming sheet 60, e.g., the pattern of applying a hot melt adhesive. In the third embodiment, the liquid impermeable backsheet 3 is bonded to the skin facing side of the exterior laminate 10, and the cuff-forming sheets 60 and the absorbent body 5 are bonded to the skin facing side of the backsheet 3 in that order. The backsheet 3 is an oblong rectangle having an approximately equal size with the absorbent body 5 and is disposed on the same place as the absorbent body 5 (i.e., in the laterally middle part of the exterior laminate 10) with its longitudinal direction coinciding with the diaper's longitudinal direction.

The backsheet 3 is bonded to the garment facing side of the cuff-forming sheets 60 so as to cover the entire area of the garment facing side of the absorbent body 5.

The term "entire area" used herein includes a substantially entire area. Specifically, when the backsheet 3 covers an area including at least 90% of the width and at least 90% of the length of the garment facing side of the absorbent body 5, the backsheet 3 is regarded as covering the entire area of the garment facing side of the absorbent body 5. When the backsheet 3 has a larger width and/or length than the width and/or length of the absorbent body 5, it is preferred that the width of the backsheet 3 be 110% or less of the width of the absorbent body 5 and, likewise, the length of the backsheet 3 be 110% or more of the length of the absorbent body 5.

In the case where the absorbent core 4 is wrapped in a water permeable cover sheet, the width and length of the absorbent body 5 are those inclusive of the cover sheet.

The outboard edges of a joint 13 between the exterior laminate 10 and the backsheet 3 (hereinafter also referred to as an exterior laminate joint 13) are outboard of joints 67 between the cuff-forming sheets 60 and the absorbent body 5.

Bonding of the backsheet 3 to the cuff-forming sheets 60 is effected by forming a backsheet joint 14 that is larger than the exterior laminate joint 13 in the width direction of the latter. Such a backsheet joint 14 provides improved liquid impermeability (leak prevention) of the cuffs 6. The backsheet 3 may be wider than the absorbent body 5, in which case the backsheet joint 14 may also be wider than the absorbent body 5.

In the third embodiment, the topsheet 2 of the diaper 1 covers the entire area of the skin facing side 4a of the absorbent core 4, the entire area of both side edge faces 4b of the absorbent core 4, and both side portions and their vicinities of the garment facing side 4c of the absorbent core 4. The topsheet 2 is bonded to the cuff-forming sheets 60 along its both side edge portions 21 similarly to the second embodiment.

In the third embodiment, the garment facing side of the side absorbent members 42 is covered with the liquid permeable topsheet 3, so that the side absorbent members 42 are capable of absorbing fluids from their garment facing side, thus providing particularly excellent leak protection. In the case where the backsheet 3 is printed with a pattern, a logo or anything, the placement of the backsheet 3 adjacent to the exterior laminate 10 produces the advantage that the print can be seen from the outside with improved visibility.

Figure 19:
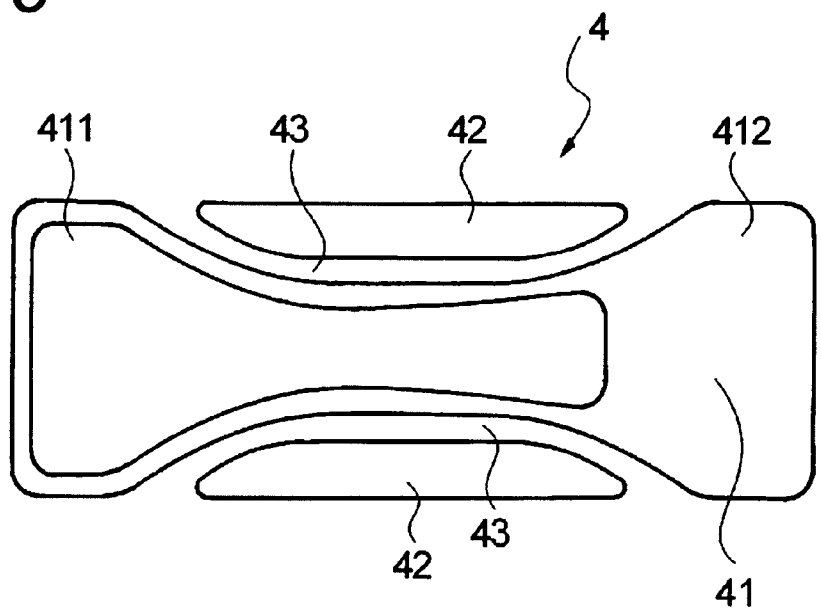
FIG. 19 is a plan of another configuration of an absorbent core according to the present invention.
Figure 20:
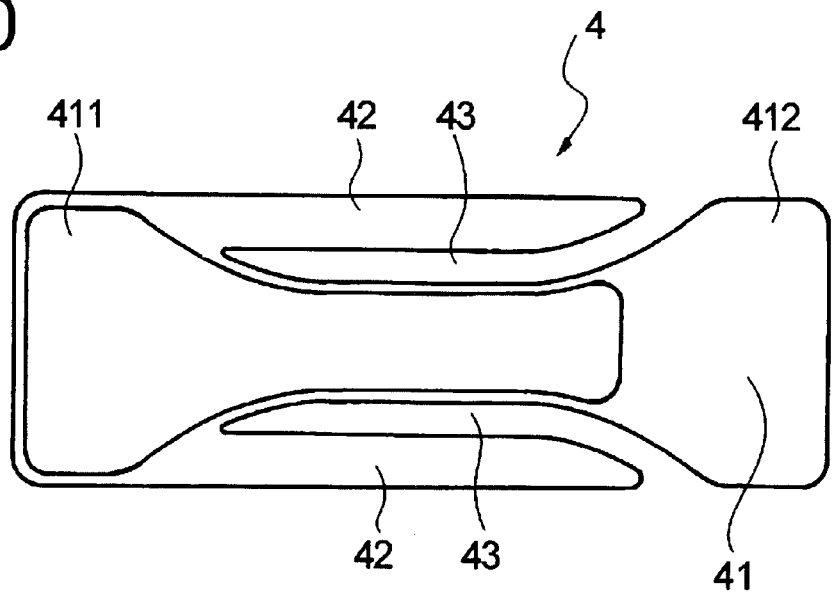
FIG. 20 is a plan of still another configuration of an absorbent core according to the present invention.
Figure 21A:
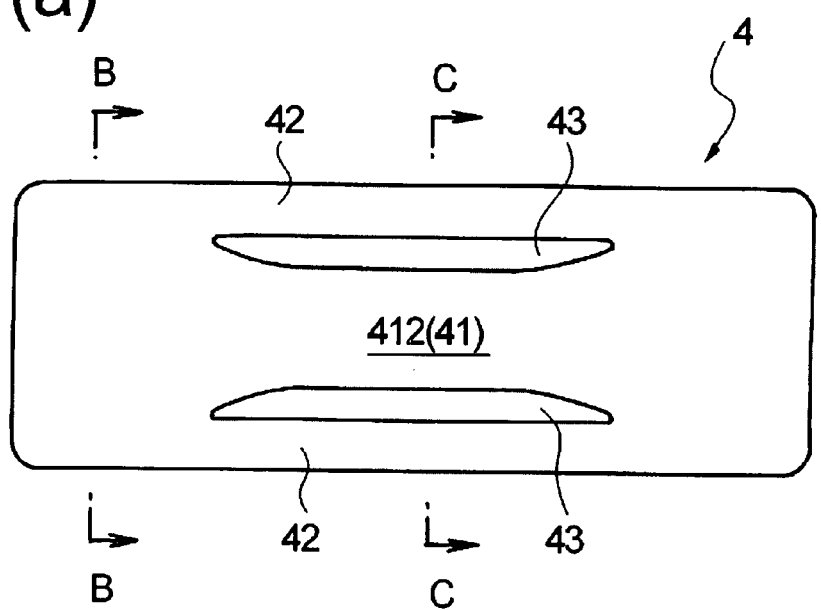
FIG. 21(a) is a plan of yet another configuration of an absorbent core according to the present invention.
Figure 21B:
FIG. 21(b) is a cross-section taken along line B-B of FIG. 21(a).
Figure 21C:
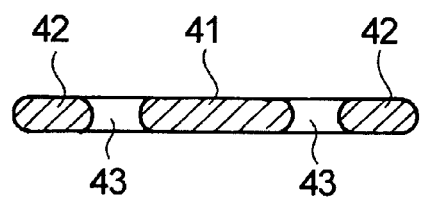
FIG. 21(c) is a cross-section taken along line C-C of FIG. 21(a).

FIGS. 19, 20, and 21(*a*) to 21(*c*) are each a plan of another configuration of the absorbent core.

The absorbent core 4 of FIG. 19 has the pair of side absorbent members 42 separated from the central absorbent member 41 so that the gaps 43 are open at their both longitudinal ends. It has otherwise the same configuration as the absorbent core 4 in the second embodiment.

The absorbent core 4 of FIG. 20 has the pair of side absorbent members 42 continuous to one longitudinal end portion of the central absorbent member 41 but discontinuous to the opposite end portion. That is, the gap 43 is open at one longitudinal end thereof. It has otherwise the same configuration as the absorbent core 4 in the second embodiment.

The disposable diaper according to the second aspect of the invention may be assembled using the absorbent core 4 shown in FIG. 19 or 20.

The absorbent core 4 shown in FIGS. 21(*a*) to 21(*c*) has its central absorbent member 41 formed solely of the lower absorbent submember 412 (a central absorbent member integral with a pair of side absorbent members 42). It has otherwise the same configuration as the absorbent core 4 in the second embodiment.

Figure 22:
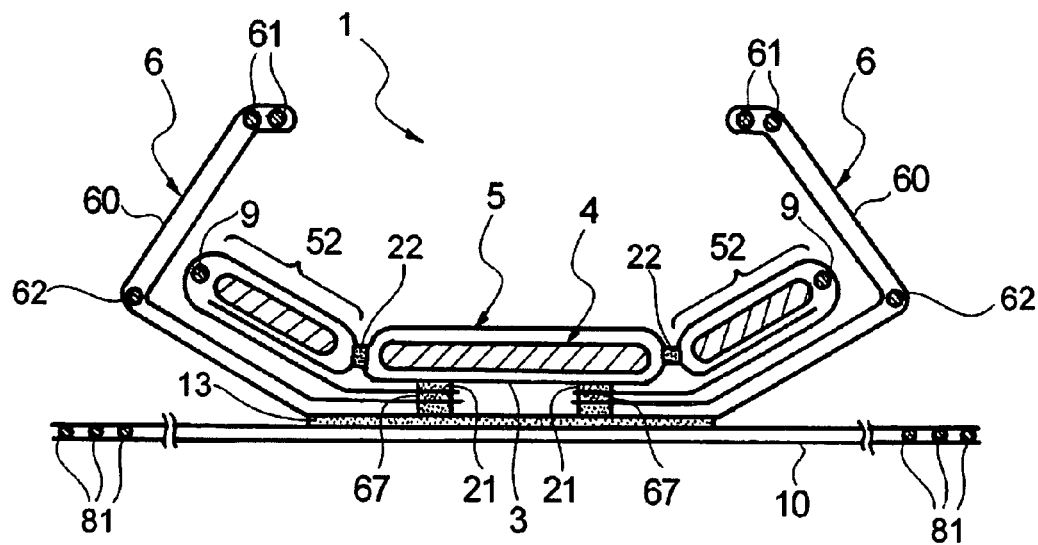
FIG. 22 is a cross-section of a fourth embodiment of the second aspect of the invention, in which the absorbent core shown in FIG. 21(a) is used, which corresponds to FIG. 5.
Figure 23:
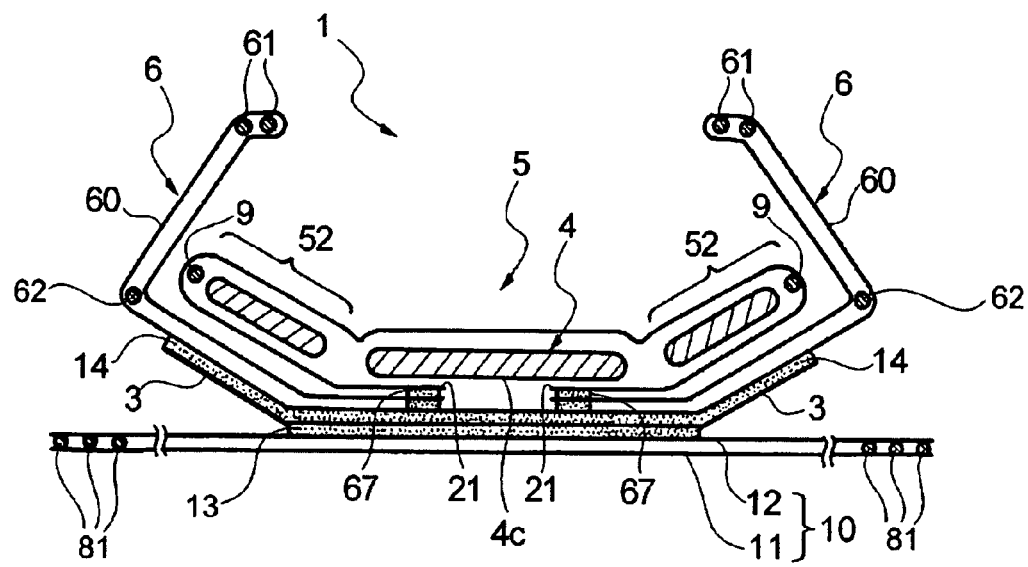
FIG. 23 is a cross-section of a fifth embodiment of the second aspect of the invention, in which the absorbent core shown in FIG. 21(a) is used, which corresponds to FIG. 5.

FIG. 22 is a view corresponding to FIG. 5, illustrating the fourth embodiment of the second aspect of the invention. FIG. 23 is a view corresponding to FIG. 5, illustrating the fifth embodiment of the second aspect of the invention. The fourth embodiment is structurally the same as the second embodiment, except for using the absorbent core 4 shown in FIGS. 21(*a*) to 21(*c*). The fifth embodiment is structurally the same as the third embodiment, except for using the absorbent core 4 shown in FIGS. 21(*a*) to 21(*c*).

While the second aspect of the present invention has been described with reference to the second to fifth embodiments, the second aspect of the invention is not construed as being limited to these embodiments, and various modifications can be made therein without departing from the spirit of the second aspect of the invention.

For instance, while in the diaper 1 of the second embodiment the side absorbent member-raising elastic members 9 are disposed over the whole length of the absorbent core 4, and the cuff-forming elastic members 61 and the cuff-drawing elastic members 62 are disposed over the whole length of the cuff-forming sheets 60, these elastic members do not always need to be disposed over the whole length of the absorbent core 4 or the cuff-forming sheets 60 as long as the desired effects are obtained. The number of the elastic members 9, 61, and 62 may be one or more per side.

In the second embodiment the central absorbent member 41 is composed of the upper absorbent submember 411 and the lower absorbent submember 412 which are dependent of each other and could be separated apart from each other. Differently, the central absorbent member may be integrally (inseparably) formed of the upper and lower absorbent submembers. It is preferred in this case that the shapes of the upper absorbent submember 411 and the lower absorbent submember 412 not be altered from those in the second embodiment and assume a superposed relation as described above and that the central absorbent member have the same regional dimensions as described above. The basis weight of the integral central absorbent member is preferably equal to the sum of the weight per unit area of the upper absorbent submember 411 and that of the lower absorbent submember 412.

While in the second embodiment the absorbent core 4 is placed with the front portion F (one longitudinal end portion) of the central absorbent member 41 located in the stomach portion A of the diaper, it may be placed with the opposite portion R of the central absorbent member located in the stomach portion.

While in the second embodiment the side absorbent member-raising elastic member 9 is provided over the whole length of each side portion of the absorbent core 4, the location of the elastic member 9 is not particularly limited as long as the side absorbent members 42 are able to rise in both sides of the absorbent core 4. For example, the elastic members 9 may be placed between the absorbent core 4 and the skin facing part of the topsheet 2 or inside the cover sheet (not shown) that totally wraps the absorbent core 4. It should be noted, however, that the elastic members 9 are preferably disposed along the side edges of the absorbent core 4 or in the vicinities thereof so that the side portions 52 of the absorbent body 5 may rise largely toward the wearer's body in the crotch portion C.

While the diaper of the second embodiment is a pull-on diaper, the present invention may be applied to a flat type disposable diaper with fastening tapes for fastening the diaper.

The constitutions of the first and second aspects of the present invention can be combined as appropriate. That is, the constitution of each embodiment of the second aspect can be incorporated into the first aspect of the invention. Conversely, the constitution of each embodiment of the first aspect can be incorporated into the second aspect of the invention.

The following is one example of such a combination. The diaper 1 according to the first aspect of the present invention is provided, which is characterized by having a pair of cuffs 6 on both sides of the absorbent body 5, each cuff 6 having the cuff-forming sheet 60 and the cuff-forming elastic member 61 fixed in its stretched state to near the free edge of the cuff-forming sheet 60, and being configured to give a higher pressure to the wearer's body in its region 91 to be applied to a body part between the iliac crests and the anterior superior iliac spines than in its waist opening portion 7 while worn. This diaper can be combined with a cross-sectional structure in which the exterior laminate 10 forming at least leg opening portions 8 is provided on the garment facing side of the absorbent body 5, and the liquid impermeable backsheet 3, the cuff-forming sheets 60, and the absorbent body 5 are successively superposed in that order on the skin facing side of the exterior laminate 10 (not shown).

In the above mentioned combination, the cross-sectional structure may be such that the backsheet 3 and cuff-forming sheets 60 are joined together by the backsheet joint 14 wider than the width of the joint 13 between the exterior laminate 10 and the backsheet 3 in the lateral direction (not shown) or such that the outboard edges of the joint 13 between the exterior laminate 10 and the backsheet 3 are positioned outboard of the joints 67 between the cuff-forming sheets 60 and the absorbent member 5 (not shown).

The above-described cross-sectional modification applied to the first aspect of the invention is application of the cross-sectional structure used in the third or fifth embodiment of the second aspect.

INDUSTRIAL APPLICABILITY

The diaper according to the first aspect of the present invention hardly slides or slips downward due to the movement of the wearer during use. The diaper hardly sags sags or droops in its crotch portion due to the weight of urine, etc. Therefore, the diaper keeps a neat appearance while worn. Since the crotch portion does not puff out excessively, the wearer's movement is not hindered by the diaper. The elastic members disposed in the diaper are prevented from excessively constricting the wearer's body, and, therefore, a wearing comfort is provided. Prevention of the diaper's sliding provides ensured protection against leakage of urine and feces.

The disposable diaper of the second aspect of the invention has cuff-drawing elastic members disposed in the leak-preventive cuffs on both sides thereof independently of the cuff-forming elastic members. Therefore, the diaper does not become baggy in the crotch during wear, keeping a neat appearance. As a result, the diaper provides a good fit and leak protection in the crotch portion and prevents the cuffs from hanging our of the leg openings.

The invention claimed is:

1. A disposable diaper which comprises an absorbent body comprising a topsheet and an absorbent core and has a waist opening portion and a pair of leg opening portion,
   a leak-preventive cuff provided on both sides of the absorbent body, each cuff comprising a cuff-forming sheet joined to the absorbent body and a cuff-forming elastic member fixed in a stretched state to near the free edge of the cuff-forming sheet, and
   an exterior laminate forming at least the leg opening portions provided on the garment facing side of the absorbent body, the exterior laminate having joined on the skin facing side thereof a liquid impermeable backsheet, the cuff-forming sheets, and the absorbent body in that order at respective joints,
   the joint between the backsheet and the cuff-forming sheets being wider than the joint between the exterior laminate and the backsheet in the lateral direction of the diaper;
   wherein the absorbent core comprises a central absorbent member and a pair of side absorbent members disposed on both sides of the central absorbent member, the central absorbent member being discrete from the pair of side absorbent members in at least the crotch portion of the diaper,
   each side absorbent member having a side absorbent member-raising elastic member which is provided near the outboard edge thereof along the longitudinal direction, so that the side absorbent member is configured to rise while the diaper is worn, and
   the diaper is configured to exert a higher pressure to the body of a wearer in a first region of the diaper adapted to be applied to a wearer's body part between the iliac crests and the anterior superior iliac spines than in the waist opening portion while worn;
   wherein the pressure of the first region is within a range of 1.1 to 2.5 kpa and the pressure of the waist opening portion is lower than the average pressure of the first region by 0.5 to 1.0 kpa.

2. The disposable diaper according to claim 1, wherein the joint between the exterior laminate and the backsheet being outboard of the joint between each cuff-forming sheet and the absorbent body.

3. The disposable diaper according to claim 1, wherein the absorbent core has a side absorbent member-raising elastic member provided on both sides thereof along the longitudinal direction, so that the absorbent body is configured to raise both side portions thereof in the crotch portion of the diaper, and each cuff further comprising a cuff-drawing elastic member provided along a position outboard of the side absorbent member-raising elastic member in a flat-out state of the diaper.

4. The disposable diaper according to claim 3, wherein the joint between the exterior laminate and the cuff-forming sheets being outboard of the joint between each cuff-forming sheet and the absorbent body.

5. The disposable diaper according to claim 3, wherein the topsheet covers the entire area of the skin facing side of the absorbent core, the entire area of both lateral side edge faces of the absorbent core, and both lateral side portions and their vicinities of the garment facing side of the absorbent core, and the topsheet is fixed on both side edge portions thereof to the respective cuff-forming sheets.

6. The disposable diaper according to claim 5, wherein the absorbent body has a liquid impermeable backsheet covering the entire area of the garment facing side of the absorbent core, the backsheet being fixedly held between the absorbent core and the portions of the topsheet that cover the lateral side portions and their vicinities of the garment facing side of the absorbent core.

7. The disposable diaper according to claim 3, wherein the joint between the exterior laminate and the backsheet being outboard of the joint between each cuff-forming sheet and the absorbent body.

* * * * *